US008420785B2

(12) United States Patent
Snider

(10) Patent No.: US 8,420,785 B2
(45) Date of Patent: Apr. 16, 2013

(54) SOLUBLE HUMAN ST-2 ANTIBODIES AND ASSAYS

(75) Inventor: James V. Snider, San Diego, CA (US)

(73) Assignee: Critical Care Diagnostics, Inc., San Diego, CA (US)

( * ) Notice: Subject to any disclaimer, the term of this patent is extended or adjusted under 35 U.S.C. 154(b) by 0 days.

(21) Appl. No.: 13/083,333

(22) Filed: Apr. 8, 2011

(65) Prior Publication Data

US 2011/0256635 A1     Oct. 20, 2011

Related U.S. Application Data

(60) Provisional application No. 61/322,578, filed on Apr. 9, 2010, provisional application No. 61/345,837, filed on May 18, 2010.

(51) Int. Cl.
| C07K 16/00 | (2006.01) |
| C12P 21/08 | (2006.01) |
| C12Q 1/68 | (2006.01) |
| G01N 33/53 | (2006.01) |

(52) U.S. Cl.
USPC ............ 530/387.1; 530/387.3; 530/388.1; 530/388.15; 435/6.19; 435/7.1; 435/7.2

(58) Field of Classification Search .................... None
See application file for complete search history.

(56) References Cited

U.S. PATENT DOCUMENTS

| 6,399,748 | B1 * | 6/2002 | Werenskiold ............ 530/388.21 |
| 7,087,396 | B2 | 8/2006 | Tominaga et al. |
| 7,432,060 | B2 | 10/2008 | Lee |
| 7,452,980 | B2 | 11/2008 | Kingsbury et al. |
| 7,655,415 | B2 | 2/2010 | Lee |
| 7,670,769 | B2 | 3/2010 | Lee |
| 7,985,558 | B2 | 7/2011 | Lee |
| 7,989,210 | B2 | 8/2011 | Lee |
| 7,998,683 | B2 | 8/2011 | Snider et al. |
| 8,090,562 | B2 | 1/2012 | Snider et al. |
| 2003/0022245 | A1 * | 1/2003 | Mills ............... 435/7.8 |
| 2003/0124624 | A1 * | 7/2003 | Tominaga et al. ............ 435/7.9 |
| 2004/0048286 | A1 | 3/2004 | Lee |
| 2005/0130136 | A1 | 6/2005 | Lee |
| 2006/0216755 | A1 | 9/2006 | Lee |
| 2007/0248981 | A1 | 10/2007 | Snider et al. |
| 2009/0192078 | A1 | 7/2009 | Lee |
| 2009/0264779 | A1 | 10/2009 | Snider et al. |
| 2009/0304699 | A1 | 12/2009 | Amatucci et al. |
| 2009/0305265 | A1 | 12/2009 | Snider et al. |
| 2010/0009356 | A1 | 1/2010 | Snider et al. |
| 2010/0159607 | A1 | 6/2010 | Lee |
| 2011/0053170 | A1 | 3/2011 | Snider et al. |
| 2011/0250703 | A1 | 10/2011 | Lee |
| 2011/0262941 | A1 | 10/2011 | Snider et al. |
| 2011/0280887 | A1 | 11/2011 | Lee |
| 2012/0040381 | A1 | 2/2012 | Snider et al. |
| 2012/0065897 | A1 | 3/2012 | Snider et al. |

FOREIGN PATENT DOCUMENTS

| WO | WO02/38794 | 5/2002 |
| WO | WO03/094856 | 11/2003 |
| WO | WO2007/127749 | 11/2007 |
| WO | WO2007130962 | 11/2007 |
| WO | WO2007/143295 | 12/2007 |
| WO | WO2009/129454 | 10/2009 |

OTHER PUBLICATIONS

U.S. Appl. No. 13/422,574, filed Mar. 16, 2012, Snider.
U.S. Appl. No. 13/552,533, filed Jul. 18, 2012, Snider et al.
International Preliminary Report on Patentability issued in PCT/US2011/031801, on Oct. 6, 2012.
International Search Report issued in PCT/US2011/03180, on Nov. 28, 2011.
Written Opinion of the International Searching Authority issued in PCT/US2011/031801, on Nov. 28, 2011.
Pascual-Figal et al., "Soluble ST2 for Predicting Sudden Cardiac Death in Patients with Chronic Heart Failure and Left Ventricular Systolic Dysfunction," Journal of the American College of Cardiology, 23:2174-2179 (2009).
MBL International Corporation, "ST2 ELISA Kit", Code No. 7638 (2001) (13 pgs) available prior to Apr. 9, 2010.
MBL International Corporation, "Anti-Hjman ST2", Code D066-3 (2 pgs) available prior to Apr. 9, 2010.
MBL International Corporation, "Anti-Human ST2", Code No. D065-3 (2 pgs) available prior to Apr. 9, 2010.
MBL International Corporation, "Anti-Human ST2", Code No. D067-3 (2 pgs.) available prior to Apr. 9, 2010.

* cited by examiner

Primary Examiner — Robert Landsman
Assistant Examiner — Ian Dang
(74) Attorney, Agent, or Firm — Fish & Richardson P.C.

(57) ABSTRACT

Provided herein are antibodies and antigen-binding antibody fragments that bind to human soluble Growth Stimulation-Expressed Gene 2 (ST2) protein, kits containing these antibodies and antibody fragments, and methods of using these antibodies and antibody fragments.

39 Claims, 13 Drawing Sheets

```
SEQUENCE LISTING

<160> NUMBER OF SEQ ID NOS: 4

<210> SEQ ID NO 1
<211> LENGTH: 328
<212> TYPE: PRT
<213> ORGANISM: Homo sapiens

<400> SEQUENCE: 1

Met Gly Phe Trp Ile Leu Ala Ile Leu Thr Ile Leu Met Tyr Ser Thr
 1               5                  10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
            180                 185                 190
```

-continued

```
Ser Val Thr Ala Thr Arg Ser Phe Thr Val Lys Asp Glu Gln Gly Phe
        195                 200                 205

Ser Leu Phe Pro Val Ile Gly Ala Pro Ala Gln Asn Glu Ile Lys Glu
    210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gly Glu Gly Gln
                260                 265                 270

Asn Gln Ser Phe Ser Asn Gly Leu Ala Cys Leu Asp Met Val Leu Arg
            275                 280                 285

Ile Ala Asp Val Lys Glu Glu Asp Leu Leu Leu Gln Tyr Asp Cys Leu
290                 295                 300

Ala Leu Asn Leu His Gly Leu Arg Arg His Thr Val Arg Leu Ser Arg
305                 310                 315                 320

Lys Asn Pro Ser Lys Glu Cys Phe
                325
```

<210> SEQ ID NO 2
<211> LENGTH: 2542
<212> TYPE: DNA
<213> ORGANISM: Homo sapiens

<400> SEQUENCE: 2

```
gaggagggac ctacaaagac tggaaactat tcttagctcc gtcactgact ccaagttcat      60
cccctctgtc tttcagtttg gttgagatat aggctactct tcccaactca gtcttgaaga     120
gtatcaccaa ctgcctcatg tgtggtgacc ttcactgtcg tatgccagtg actcatctgg     180
agtaatctca acaacgagtt accaatactt gctcttgatt gataaacaga atggggtttt     240
ggatcttagc aattctcaca attctcatgt attccacagc agcaaagttt agtaaacaat     300
catgggcct ggaaaatgag gctttaattg taagatgtcc tagacaagga aaacctagtt      360
acaccgtgga ttggtattac tcacaaacaa acaaaagtat tcccactcag gaaagaaatc     420
gtgtgtttgc ctcaggccaa cttctgaagt ttctaccagc tgcagttgct gattctggta     480
tttatacctg tattgtcaga agtcccacat tcaataggac tggatatgcg aatgtcacca     540
tatataaaaa acaatcagat tgcaatgttc cagattattt gatgtattca acagtatctg     600
gatcagaaaa aaattccaaa atttattgtc ctaccattga cctctacaac tggacagcac     660
ctcttgagtg gtttaagaat tgtcaggctc ttcaaggatc aaggtacagg gcgcacaagt     720
cattttggt cattgataat gtgatgactg aggacgcagg tgattacacc tgtaaattta     780
tacacaatga aaatggagcc aattatagtg tgacggcgac caggtccttc acggtcaagg     840
atgagcaagg ctttttctctg tttccagtaa tcggagcccc tgcacaaaat gaaataaagg     900
aagtggaaat tggaaaaac gcaaacctaa cttgctctgc ttgttttgga aaaggcactc     960
agttcttggc tgccgtcctg tggcagctta atggaacaaa attacagac tttggtgaac    1020
caagaattca acaagaggaa gggcaaaatc aaagtttcag caatgggctg gcttgtctag    1080
acatggtttt aagaatagct gacgtgaagg aagaggattt attgctgcag tacgactgtc    1140
tggccctgaa tttgcatggc ttgagaaggc acaccgtaag actaagtagg aaaaatccaa    1200
gtaaggagtg tttctgagac tttgatcacc tgaactttct ctagcaagtg taagcagaat    1260
ggagtgtggt tccaagagat ccatcaagac aatgggaatg cctgtgcca taaaatgtgc     1320
ttctcttctt cgggatgttg tttgctgtct gatctttgta gactgttcct gtttgctggg    1380
```

-continued

```
agcttctctg ctgcttaaat tgttcgtcct cccccactcc ctcctatcgt tggtttgtct    1440
agaacactca gctgcttctt tggtcatcct tgttttctaa ctttatgaac tccctctgtg    1500
tcactgtatg tgaaaggaaa tgcaccaaca accgtaaact gaacgtgttc ttttgtgctc    1560
ttttataact tgcattacat gttgtaagca tggtccgttc tataccttttt tctggtcata   1620 atgaacactc attttgttag cgagggtggt aaagtgaaca aaagggggaa gtatcaaact    1680
actgccattt cagtgagaaa atcctaggtg ctactttata ataagacatt tgttaggcca    1740
ttcttgcatt gatataaaga aatacctgag actgggtgat ttatatgaaa agaggtttaa    1800
ttggctcaca gttctgcagg ctgtatggga agcatggcgg catctgcttc tggggacacc    1860
tcaggagctt tactcatggc agaaggcaaa gcaaggcag gcacttcaca cagtaaaagc     1920
aggagcgaga gagaggtgcc acactgaaac agccagatct catgagaagt cactcactat    1980
tgcaaggaca gcatcaaaga gatggtgcta aaccattcat gatgaactca ccccatgat    2040 ccaatcacct cccaccaggc tccacctcga atactgggga ttaccattca gcatgagatt   2100
tgggcaggaa cacagaccca aaccatacca cacacattat cattgttaaa ctttgtaaag   2160
tatttaaggt acatggaaca cacgggaagt ctggtagctc agcccatttc tttattgcat   2220
ctgttattca ccatgtaatt caggtaccac gtattccagg gagcctttct tggccctcag   2280
tttgcagtat acacactttc caagtactct tgtagcatcc tgtttgtatc atagcactgg   2340
tcacattgcc ttacctaaat ctgtttgaca gtctgctcaa cacgactgca agctccatga   2400
gggcagggac atcatctctt ccatctttgg gtccttagtg caatacctgg cagctagcca   2460
gtgctcagct aaatatttgt tgactgaata aatgaatgca caaccaaaaa aaaaaaaaaa   2520
aaaaaaaaaa aaaaaaaaaa aa                                            2542

<210> SEQ ID NO 3
<211> LENGTH: 556
<212> TYPE: PRT
<213> ORGANISM: Homo sapiens

<400> SEQUENCE: 3

Met Gly Phe Trp Ile Leu Ala Ile Leu Thr Ile Leu Met Tyr Ser Thr
 1               5                  10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175
```

Gly Asp Tyr Thr Cys Lys Phe Ile His Asn Glu Asn Gly Ala Asn Tyr
            180                 185                 190

Ser Val Thr Ala Thr Arg Ser Phe Thr Val Lys Asp Glu Gln Gly Phe
195                 200                 205

Ser Leu Phe Pro Val Ile Gly Ala Pro Ala Gln Asn Glu Ile Lys Glu
210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
            260                 265                 270

Asn Gln Ser Phe Ser Asn Gly Leu Ala Cys Leu Asp Met Val Leu Arg
        275                 280                 285

Ile Ala Asp Val Lys Glu Glu Asp Leu Leu Leu Gln Tyr Asp Cys Leu
    290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ala Val Cys
                325                 330                 335

Ser Val Phe Leu Met Leu Ile Asn Val Leu Ile Ile Leu Lys Met
        340                 345                 350

Phe Trp Ile Glu Ala Thr Leu Leu Trp Arg Asp Ile Ala Lys Pro Tyr
                355                 360                 365

Lys Thr Arg Asn Asp Gly Lys Leu Tyr Asp Ala Tyr Val Val Tyr Pro
370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                405                 410                 415

Leu Cys Ile Tyr Gly Arg Asp Met Leu Pro Gly Glu Asp Val Val Thr
            420                 425                 430

Ala Val Glu Thr Asn Ile Arg Lys Ser Arg Arg His Ile Phe Ile Leu
        435                 440                 445

Thr Pro Gln Ile Thr His Asn Lys Glu Phe Ala Tyr Glu Gln Glu Val
450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                485                 490                 495

Gln Asp Ser Leu Gln His Leu Met Lys Val Gln Gly Thr Ile Lys Trp
            500                 505                 510

Arg Glu Asp His Ile Ala Asn Lys Arg Ser Leu Asn Ser Lys Phe Trp
        515                 520                 525

Lys His Val Arg Tyr Gln Met Pro Val Pro Ser Lys Ile Pro Arg Lys
530                 535                 540

Ala Ser Ser Leu Thr Pro Leu Ala Ala Gln Lys Gln
545                 550                 555

<210> SEQ ID NO 4
<211> LENGTH: 2058
<212> TYPE: DNA
<213> ORGANISM: Homo sapiens

```
<400> SEQUENCE: 4
aaagagaggc tggctgttgt atttagtaaa gctataaagc tgtaagagaa attggctttc      60
tgagttgtga aactgtgggc agaaagttga ggaagaaaga actcaagtac aacccaatga     120
ggttgagata taggctactc ttcccaactc agtcttgaag agtatcacca actgcctcat     180
gtgtggtgac cttcactgtc gtatgccagt gactcatctg gagtaatctc aacaacgagt     240
taccaatact tgctcttgat tgataaacag aatggggttt tggatcttag caattctcac     300
aattctcatg tattccacag cagcaaagtt tagtaaacaa tcatggggcc tggaaaatga     360
ggctttaatt gtaagatgtc ctagacaagg aaaacctagt tacaccgtgg attggtatta     420
ctcacaaaca aacaaaagta ttcccactca ggaaagaaat cgtgtgtttg cctcaggcca     480
acttctgaag tttctaccag ctgcagttgc tgattctggt attttatacct gtattgtcag     540 aagtcccaca ttcaatagga ctggatatgc gaatgtcacc atatataaaa aacaatcaga     600
ttgcaatgtt ccagattatt tgatgtattc aacagtatct ggatcagaaa aaaattccaa     660
aatttattgt cctaccattg acctctacaa ctggacagca cctcttgagt ggtttaagaa     720
ttgtcaggct cttcaaggat caaggtacag ggcgcacaag tcattttggg tcattgataa     780
tgtgatgact gaggacgcag gtgattacac ctgtaaattt atacacaatg aaaatggagc     840
caattatagt gtgacggcga ccaggtcctt cacggtcaag gatgagcaag cttttctct     900 gtttccagta atcggagccc ctgcacaaaa tgaaataaag gaagtggaaa ttggaaaaaa     960
cgcaaaccta acttgctctg cttgttttgg aaaaggcact cagttcttgg ctgccgtcct    1020
gtggcagctt aatggaacaa aaattacaga ctttggtgaa ccaagaattc aacaagagga    1080
agggcaaaat caaagtttca gcaatgggct ggcttgtcta gacatggttt taagaatagc    1140
tgacgtgaag gaagaggatt tattgctgca gtacgactgt ctggccctga atttgcatgg    1200
cttgagaagg cacaccgtaa gactaagtag gaaaaatcca attgatcatc atagcatcta    1260
ctgcataatt gcagtatgta gtgtattttt aatgctaatc aatgtcctgg ttatcatcct    1320
aaaaatgttc tggattgagg ccactctgct ctggagagac atagctaaac cttacaagac    1380
taggaatgat ggaaagctct atgatgctta tgttgtctac ccacggaact acaaatccag    1440
tacagatggg gccagtcgtg tagagcactt tgttcaccag attctgcctg atgttcttga    1500
aaataaatgt ggctatacct tatgcattta tgggagagat atgctacctg agaagatgt    1560 agtcactgca gtggaaacca acatacgaaa gagcaggcgg cacattttca tcctgacccc    1620
tcagatcact cacaataagg agtttgccta cgagcaggag gttgccctgc actgtgccct    1680
catccagaac gacgccaagg tgatacttat tgagatggag gctctgagcg agctggacat    1740
gctgcaggct gaggcgcttc aggactccct ccagcatctt atgaaagtac aggggaccat    1800
caagtggagg gaggaccaca ttgccaataa aaggtccctg aattctaaat tctggaagca    1860
cgtgaggtac caaatgcctg tgccaagcaa aattcccaga aaggcctcta gtttgactcc    1920
cttggctgcc cagaagcaat agtgcctgct gtgatgtgca aaggcatctg agtttgaagc    1980
tttcctgact tctcctagct ggcttatgcc cctgcactga agtgtgagga gcaggaatat    2040
taaagggatt caggcctc                                                  2058
```

SOLUBLE HUMAN ST-2 ANTIBODIES AND ASSAYS

CROSS-REFERENCE TO RELATED APPLICATIONS

This application claims priority to U.S. provisional application 61/322,578, filed Apr. 9, 2010, and U.S. provisional application 61/345,837, filed May 18, 2010, the contents of each of which are incorporated herein by reference in their entirety.

TECHNICAL FIELD

Described herein are antibodies and antigen-binding fragments of antibodies that bind to human soluble Growth Stimulation-Expressed Gene 2 (ST2) protein, kits containing these antibodies and antibody fragments, and assays using these antibodies and antibody fragments.

BACKGROUND

ST2 is an interleukin-1 receptor family member with transmembrane (ST2L) and soluble isoforms (sST2 or soluble ST2) (Iwahana et al., *Eur. J. Biochem.* 264:397-406, 1999). Recently published articles describe the current knowledge on the relationship of ST2 to inflammatory diseases (Arend et al., *Immunol. Rev.* 223:20-38, 2008; Kakkar et al., *Nat. Rev. Drug Discov.* 7:827-840, 2008; Hayakawa et al., *J. Biol. Chem.* 282:26369-26380, 2007; Trajkovic et al., *Cytokine Growth Factor Rev.* 15:87-95, 2004). Circulating concentrations of human soluble ST2 are elevated in patients suffering from various disorders associated with an abnormal type-2 T helper cell (Th2) response, including systemic lupus erythematosus and asthma, as well as in inflammatory conditions that are mainly independent of a Th2 response, such as septic shock or trauma (Trajkovic et al., *Cytokine Growth Factor Rev.* 15:87-95, 2004; Brunner et al., *Intensive Care Med.* 30:1468-1473, 2004). Furthermore, interleukin-33/ST2L signaling represents a crucial cardioprotective mechanism in case of mechanical overload (Seki et al., *Circulation Heart Fail.* 2:684-691, 2009; Kakkar et al., *Nat. Rev. Drug Discov.* 7:827-40, 2008; Sanada et al., *J. Clin. Invest.* 117:1538-1549, 2007). An elevation in human soluble ST2 is also predictive of worse prognosis in patients with heart failure (HF) and those with myocardial infarction (Kakkar et al., *Nat. Rev. Drug Discov.* 7:827-40, 2008; Weinberg et al., *Circulation* 107:721-726, 2003; Shimpo et al., *Circulation* 109:2186-2190, 2004; Januzzi et al., *J. Am. Coll. Cardiol.* 50:607-613, 2007; Mueller et al., *Clin. Chem.* 54:752-756, 2008; Rehman et al., *J. Am. Coll. Cardiol.* 52:1458-65, 2008; Sabatine et al., *Circulation* 117:1936-1944, 2008). Elevated levels of human soluble ST2 are also predictive for death of a subject within one year (see, for example, WO 07/127,749). Taken together, human soluble ST2 has been implicated in certain inflammatory diseases and the cardioprotective paracrine system, and is a predictive marker for prognosis in patients with heart failure and for death of a subject within one year.

SUMMARY

The present invention is based, at least in part, on the development of new antibodies specific for human soluble ST2 protein. These antibodies and antigen-binding fragments thereof are useful, e.g., for the quantitation of human soluble ST2 proteins in biological samples (e.g., clinical samples), for predicting the risk of death within one year in a subject, for determining whether to discharge or to initiate or continue therapeutic treatment (e.g., inpatient treatment) of a subject, and for selecting a subject for participation in a clinical study. Provided herein are these antibodies and antigen-binding fragments thereof, kits containing these antibodies and antibody fragments, and various methods of using these antibodies and antibody fragments.

Provided herein are isolated antibodies and antigen-binding fragments thereof that are, or bind competitively with, an antibody produced from the hybridomas deposited at the American Type Culture Collection (ATTC) and designated by Patent Deposit Designation PTA-10431 and PTA 10432. In some embodiments, the antibody or fragment thereof does not bind competitively with either or both of a D066-3 or a D067-3 antibody (MBL International) (described in U.S. Pat. No. 7,087,396), or has a $K_D$ for binding to human soluble ST2 equal to or less than $1.51 \times 10^{-9}$ M. In some embodiments, the antibody or fragment thereof has a $K_D$ for binding to human soluble ST2 equal to or less than $8.59 \times 10^{-10}$ M. In some embodiments, the antibody or fragment thereof is chimeric or is humanized. In some embodiments, the fragment is selected from the group of: a Fab fragment, a $F(ab')_2$ fragment, and a scFv fragment. In some embodiments, the antibody or fragment thereof is glycosylated. In some embodiments, the antibody or fragment thereof contains one or more complementary determining regions of the light or heavy chain of the antibody produced by the hybridoma deposited at the ATCC and designated by the Patent Deposit Designation PTA-10431 or PTA-10432. In some embodiments, the antibody is an antibody produced by the hybridoma deposited at the ATCC and designed by the Patent Deposit Designation PTA-10431, or an antigen-binding fragment thereof, or an antibody produced by the hybridoma deposited at the ATCC and designated by the Patent Deposit Designation PTA-10432, or an antigen-binding fragment thereof.

Also provided are isolated antibodies and antigen-binding fragments thereof that specifically bind to human soluble ST2, wherein the antibodies and antigen-binding fragments thereof were produced by a process that includes immunizing a non-human mammal (e.g., mouse, rat, rabbit, goat, cow, pig, monkey, or horse) with a recombinant human soluble ST2 isolated from a human cell (e.g., a human fibroblast, neuronal, epithelial, or endothelial cell, an embryonic or adult cell, especially a human embryonic kidney cell). In some embodiments, the recombinant human soluble ST2 isolated is fully glycosylated, i.e., has substantially the same glycosylation as a native endogenous human soluble ST2 present in human serum. In some embodiments of all of the antibodies and fragments described herein, the antibody or fragment thereof is labeled.

Also provided are cells of the hybridoma deposited at the ATCC and designated by the Patent Deposit Designation PTA-10431 and cells of the hybridoma deposited at the ATCC and designated by the Patent Deposit Designation PTA-10432.

Also provided are methods of quantitating a level of human soluble ST2 in a sample from a subject. The methods include contacting the sample with at least one antibody or fragment thereof described herein, and detecting binding of the antibody or fragment thereof to human soluble ST2. In some embodiments, the method includes the use of at least two different antibodies or fragments thereof described herein.

Also provided are methods of predicting the risk of death within one year in a subject. The methods include obtaining a sample from a subject and determining the level of human soluble ST2 using at least one antibody or fragment thereof described herein, where an elevated level of human soluble ST2 in the sample compared to a reference level of human soluble ST2 indicates that the subject has an increased risk of death within one year (e.g., increased risk of death within one year relative to a subject (e.g., a subject having the same disease) that has decreased level or substantially the same level of human soluble ST2 relative to the same control), and a decreased level or substantially the same level of human soluble ST2 indicates that the subject has a decreased risk of death within one year (e.g., a decreased risk of death within one year relative to a subject (e.g., a subject having the same disease) that has an increased level or substantially the same level of human soluble ST2 relative to the same control).

Also provided are methods of determining whether to discharge an inpatient or to initiate or continue treatment of a subject on an inpatient basis including obtaining a sample from a subject and determining the level of human soluble ST2 in the sample using at least one antibody or fragment described herein, where an elevated level of human soluble ST2 in the sample compared to a reference level of human soluble ST2 indicates that inpatient treatment should be initiated or continued, and a decreased or an equal level of human soluble ST2 indicates that the subject should be considered for discharge. In some embodiments, the subject has at least one or more of the following symptoms: chest pain or discomfort, shortness of breath, nausea, vomiting, eructation, sweating, palpitations, lightheadedness, fatigue, and fainting.

Also provided are methods of selecting a subject for participation in a clinical study including obtaining a sample from a subject, determining the level of human soluble ST2 in the sample using at least one antibody or fragment thereof described herein, and selecting the subject for participation in a clinical study if the subject's level of human soluble ST2 relative to a reference level of human soluble ST2 indicates that the subject should be selected for participation in a clinical study. In some embodiments, the presence of an elevated level of human soluble ST2 indicates that the subject should be selected for participation in a clinical study.

Also provided are methods for selecting a therapeutic treatment for a subject including determining a level of human soluble ST2 in a biological sample from the subject using at least one antibody or fragment thereof described herein, wherein the subject's level of human soluble ST2 relative to a reference level of human soluble ST2 is used to select a therapeutic treatment for the subject. In some embodiments, the presence of an elevated level of human soluble ST2 is used to select the therapeutic treatment for the subject.

In some embodiments of any of the methods described herein, the subject is undiagnosed or is not presenting with two or more (e.g., at least three, four, or five) symptoms of a disease state; the subject has been diagnosed as having a disease (e.g., heart failure, coronary artery disease, cardiovascular disease, acute coronary syndrome, renal insufficiency, stroke, or any of the diseases described herein); or the subject has one or more of: hypertriglyceridemia, hypercholesterolemia, hypertension, and a body mass index of $\geq 30$. In some embodiments of any of the methods described herein, the determining is performed using at least two antibodies or fragments thereof described herein.

In some embodiments of any of the methods described herein, the reference level of human soluble ST2 is a threshold level of human soluble ST2. In some embodiments, the threshold level is an average level of human soluble ST2 in a healthy patient population (e.g., a healthy male patient population or a healthy female patient population). In some embodiments of any of the methods described herein, the reference level is a level of human soluble ST2 present in a sample of a subject not presenting with two or more symptoms of disease, a subject not diagnosed as having a disease, or a subject not identified as being at risk for developing a disease.

In any of the methods described herein, the subject has not been diagnosed as having a disease (e.g., heart failure, coronary artery disease, cardiovascular disease, acute coronary artery disease, acute coronary syndrome, renal insufficiency, or stroke, or any of the diseases described herein). In any of the methods described herein, the sample contains blood, serum, or plasma. Any of the antibodies and fragments thereof described herein can be used in any of methods described herein.

Also provided are methods of diagnosing a disease in a subject including obtaining a sample from a subject, determining a level of human soluble ST2 in the sample using at least one antibody or fragment thereof described herein and a level of at least one additional marker, wherein an elevated level of human soluble ST2 in the sample compared to a reference level of human soluble ST2 and an altered level of the at least one additional marker relative to a reference level of the at least one additional marker, indicate that the subject has the disease (e.g., cardiovascular disease, a pulmonary disease, sepsis, Kawasaki disease, or a Th2-associated disease, or any of the other diseases described herein).

Also provided are methods for determining whether a subject has a normal human soluble ST2 level (and thus is likely to be free from severe disease, e.g., cardiovascular disease, and a normal risk of death or hospitalization, e.g., within one year) including obtaining a sample from a subject and determining the level of human soluble ST2 in the sample, wherein the subject is determined to have a normal human soluble ST2 level if the level of human soluble ST2 falls in a specific range (e.g., between about 14.5 to about 25.3 ng/mL, or between about 18.1 to about 19.9 ng/mL). In some embodiments, a male subject is determined to have a normal human soluble ST2 level if the level of human soluble ST2 is between any range listed in Table 9. In some embodiments, a female subject is determined to have a normal human soluble ST2 if the level of human soluble ST2 is between any range listed in Table 9.

Also provided are kits containing at least one (e.g., two, three, four, or five) of the antibodies or antigen-binding fragments thereof described herein. Some embodiments of these kits contain two antibodies or antigen-binding fragments thereof described herein. In some embodiments of these kits, at least one of the antibodies or fragments thereof has a $K_D$ for binding to human soluble ST2 (e.g., recombinant human soluble ST2) equal to or less than $8.59 \times 10^{-10}$ M. In some embodiments, the kit is provided as an enzyme-linked immunosorbent assay (ELISA). In some embodiments, the kit further contains a recombinant human soluble ST2 isolated from a human cell (e.g., a human embryonic kidney cell). In some embodiments, the recombinant human soluble ST2 is fully glycosylated.

By the term "soluble ST2" is meant a soluble protein containing a sequence at least 90% identical (e.g., at least 95%, 96%, 97%, 98%, 99%, or 100% identical) to NCBI Accession No. NP_003847.2 (SEQ ID NO: 1) or a nucleic acid containing a sequence at least 90% identical (e.g., at least 95%, 96%, 97%, 98%, 99%, or 100% identical) to NCBI Accession No. NM_003856.2 (SEQ ID NO: 2).

By the term "elevated" or "elevation" is meant a difference, e.g., a statistically significant difference (e.g., an increase) in a determined or measured level (e.g., a human soluble ST2 protein level) compared to a reference level (e.g., a level of human soluble ST2 in a subject not having a disease, a subject not presenting with two or more symptoms of a disease, or a subject not identified as being at risk of developing a disease, or a threshold level of human soluble ST2). In some embodiments, the reference is a threshold level, and any level above that is considered "elevated." Additional reference levels of human soluble ST2 are described herein.

By the term "health care facility" is meant a location where a subject can receive medical care from a health care professional (e.g., a nurse, a physician, or a physician's assistant). Non-limiting examples of health care facilities include hospitals, clinics, and assisted care facilities (e.g., a nursing home).

By the term "inpatient" is meant a subject that is admitted to a medical care facility (e.g., a hospital or an assisted care facility).

By the term "inpatient treatment" is meant the monitoring and/or medical treatment of a subject that is admitted to a health care facility (e.g., a hospital or assisted care facility). For example, a subject receiving inpatient treatment may be administered one or more therapeutic agents by a health care profession or may undergo a medical procedure (e.g., surgery (e.g., organ transplant, heart bypass surgery), angioplasty, imaging (e.g., magnetic resonance imaging, ultrasound imaging, and computer tomography scanning)). In other examples, one or more marker of a disease or the severity of the condition can be periodically measured by a health care professional to assess the severity or progression of disease or the subject's condition.

By the term "reference level" is meant a threshold level or a level in a control subject or control patient population. A reference level will depend on the assay performed and can be determined by one of ordinary skill in the art. A reference level can be a baseline level or a level in the same patient measured at an earlier or later point in time. Some non-limiting examples of reference levels of human soluble ST2 include the level of human soluble ST2 in a subject that: has not been diagnosed as having a disease; does not present with at least two or more symptoms of a disease; does not have high risk CVD; does not have renal failure; does not have hypertriglyceridemia, hypercholesterolemia, hypertension, and/or a body mass index of <30 (e.g., a BMI under 25); is not at risk of developing a disease; and/or does not suffer from a disease associated with increased ST2 levels (e.g., cardiovascular disease, a pulmonary disease, sepsis, Kawasaki disease, or a Th2-associated disease, or any of the other diseases described herein). Additional control patient populations are described herein. Additional examples of reference levels of human soluble ST2 are threshold levels of human soluble ST2. Reference levels of human soluble ST2 can be determined using methods known in the art; some exemplary levels are described herein.

In some embodiments, a ratio of two human soluble ST2 levels in a subject is calculated. The reference ratio can be compared to a reference ratio of human soluble ST2 levels measured in a subject (e.g., any of the control subjects described herein or the same subject), for example, a reference ratio can be a ratio of the levels of human soluble ST2 before and after onset of a disease (e.g., cardiac disease (e.g., heart failure, coronary artery disease, cardiovascular disease, acute coronary syndrome, and angina), renal insufficiency, or stroke, or any of the other diseases associated with increased human soluble ST2 levels as described herein) symptoms; a ratio of the levels of human soluble ST2 before and after diagnosis with disease (e.g., cardiac disease (e.g., heart failure, coronary artery disease, cardiovascular disease, acute coronary syndrome, and angina), renal insufficiency, or stroke, or any of the other diseases described herein); a ratio of the levels of ST2 before and after therapeutic treatment for a disease ((e.g., cardiac disease (e.g., heart failure, coronary artery disease, cardiovascular disease, acute coronary syndrome, and angina), renal insufficiency, or stroke, or any of the other diseases described herein); a ratio of the human soluble ST2 levels at two different time points during therapeutic treatment (e.g., inpatient or outpatient treatment) for a disease (e.g., cardiac disease (e.g., heart failure, coronary artery disease, cardiovascular disease, acute coronary syndrome, and angina), renal insufficiency, or stroke, or any of the other diseases described herein); or a ratio of the human soluble ST2 levels before and after a cardiac event (e.g., a myocardial infarction).

In some embodiments, the ratio of the levels of human soluble ST2 measured in a subject can be compared to a threshold reference ratio. Reference ratios of human soluble ST2 can be determined using methods known in the art; reference ratios of human soluble ST2 can be calculated using the data described herein. For example, reference ratio of human soluble ST2 may be between about 0.7 and about 1.1, or about 1.

By the term "therapeutic treatment" or "treatment" is meant the administration of one or more pharmaceutical agents to a subject or the performance of a medical procedure on the body of a subject (e.g., surgery, such as organ transplant or heart surgery). Non-limiting examples of pharmaceutical agents that can be administered to a subject include nitrates, calcium channel blockers, diuretics, thrombolytic agents, digitalis, renin-angiotensin-aldosterone system (RAAS) modulating agents (e.g., beta-adrenergic blocking agents, angiotensin-converting enzyme inhibitors, aldosterone antagonists, renin inhibitors, and angiotensin II receptor blockers), and cholesterol-lowering agents (e.g., a statin). The term therapeutic treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

As used herein, a "subject" is a mammal, e.g., a human.

As used herein, a "biological sample" includes one or more of blood, serum, plasma, urine, and body tissue. Generally, a biological sample is a sample containing serum, blood, or plasma.

As used herein, the term "antibody" refers to a protein that generally contains heavy chain polypeptides and light chain polypeptides. Antigen recognition and binding occurs within the variable regions of the heavy and light chains. Single domain antibodies having one heavy chain and one light chain, and heavy chain antibodies devoid of light chains, are also known. A given antibody comprises one of five different types of heavy chains, called alpha, delta, epsilon, gamma, and mu, the categorization of which is based on the amino acid sequence of the heavy chain constant region. These different types of heavy chains give rise to five classes of antibodies, IgA (including IgA1 and IgA2), IgD, IgE, IgG (IgG1, IgG2, IgG3, and IgG4) and IgM, respectively. A given antibody also comprises one of two types of light chains, called kappa or lambda, the categorization of which is based on the amino acid sequence of the light chain constant domains. IgG, IgD, and IgE antibodies generally contain two identical heavy chains and two identical light chains and two antigen combining domains, each composed of a heavy chain variable region (VH) and a light chain variable region (VL). Generally IgA antibodies are composed of two monomers, each monomer composed of two heavy chains and two light chains (as for IgG, IgD, and IgE antibodies). In this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies). In this way the secreted IgM molecule has ten antigen-binding domains, each again composed of a VH and a VL. A cell surface form of IgM also exists and this has a two heavy chain/two light chain structure similar to IgG, IgD, and IgE antibodies.

As used herein, the term "chimeric antibody" refers to an antibody that has been engineered to comprise at least one human constant region. For example, one or all (e.g., one, two, or three) of the variable regions of the light chain(s) and/or one or all (e.g., one, two, or three) of the variable regions the heavy chain(s) of a mouse antibody (e.g., a mouse monoclonal antibody) can each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies, and will also be aware of suitable techniques for their generation. See, for example, U.S. Pat. Nos. 4,816,567; 4,978,775; 4,975,369; and U.S. Pat. No. 4,816,397.

As used herein, the term "fully human antibodies" are antibodies or antigen binding fragments of antibodies that contain only human-derived amino acid sequences. For example, a fully human antibody may be produced from a human B-cell or a human hybridoma cell. In additional embodiments, the antibody may be produced from a transgenic animal that contains the locus for a human heavy chain immunoglobulin and a human light chain immunoglobulin, or contains a nucleic acid that encodes the heavy and light chains of a specific human antibody.

"Complementarity-determining region" or "CDR" as the terms are used herein refer to short polypeptide sequences within the variable region of both heavy and light chain polypeptides that are primarily responsible for mediating specific antigen recognition. CDRs have been described by Kabat, et al., *J. Biol. Chem.* 252, 6609-6616, 1977; Chothia et al., *J. Mol. Biol.* 196:901-917, 1987; and MacCallum et al., *J. Mol. Biol.* 262:732-745, 1996. There are three CDRs (termed CDR1, CDR2, and CDR3) within each VL and each VH.

"Fragment" or "antibody fragment" as the terms are used herein refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments can include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

"Framework region" as the term is used herein refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

"Humanized antibody" as the term is used herein refers to an antibody that has been engineered to comprise one or more human framework regions in the variable region together with non-human (e.g., mouse, rat, or hamster) complementarity-determining regions (CDRs) of the heavy and/or light chain. In some embodiments, a humanized antibody comprises sequences that are entirely human except for the CDR regions. Humanized antibodies are typically less immunogenic to humans, relative to non-humanized antibodies, and thus offer therapeutic benefits in certain situations. Humanized antibodies are known in the art, and suitable techniques for generating humanized antibodies are also known. See for example, Hwang et al., *Methods* 36:35, 2005; Queen et al., *Proc. Natl. Acad. Sci. U.S.A.* 86:10029-10033, 1989; Jones et al., *Nature* 321:522-25, 1986; Riechmann et al., *Nature* 332:323-27, 1988; Verhoeyen et al., *Science* 239:1534-36, 1988; Orlandi et al., *Proc. Natl. Acad. Sci. U.S.A.* 86:3833-3837, 1989; U.S. Pat. Nos. 5,225,539; 5,530,101; 5,585,089; 5,693,761; 5,693,762; and 6,180,370; and WO 90/07861.

As used herein, the term "Th2-associated disease" refers to a disease associated with an abnormal type-2 T helper cell (Th2) response.

As used herein, the term "cardiovascular disease" refers to a disorder of the heart and blood vessels, and includes disorders of the arteries, veins, arterioles, venules, and capillaries.

As used herein, the term "pulmonary disease" refers to a disorder of the lungs.

By the term "additional marker" is meant a protein, nucleic acid, lipid, or carbohydrate, or a combination (e.g., two or more) thereof, that is diagnostic of the presence of a particular disease. The methods described herein for diagnosing a subject as having a disease can include detecting a level of soluble human ST2 and at least one additional marker in a sample from the subject. Several additional markers useful for the diagnosis of disease are known in the art (e.g., proANP, NT-proANP, ANP, proBNP, NT-proBNP, BNP, troponin, CRP, creatinine, Blood Urea Nitrogen (BUN), liver function enzymes, albumin, and bacterial endotoxin; and those markers described in U.S. Patent Application Nos.: 2007/0248981; 2011/0053170; 2010/0009356; 2010/0055683; 2009/0264779; each of which is hereby incorporated by reference).

By the term "hypertriglyceridemia" is meant a triglyceride level that is greater than or equal to 180 ng/mL (e.g., greater than or equal to 200 ng/mL).

By the term "hypercholesterolemia" is meant an increased level of at least one form of cholesterol or total cholesterol in a subject. For example, a subject with hypercholesterolemia can have a high density lipoprotein (HDL) level of $\geq 40$ mg/dL (e.g., $\geq 50$ mg/dL or $\geq 60$ mg/mL), a low density lipoprotein (LDL) level of $\geq 130$ mg/dL (e.g., $\geq 160$ mg/dL or $\geq 200$ mg/dL), and/or a total cholesterol level of $\geq 200$ mg/dL (e.g., 240 mg/dL).

By the term "hypertension" is meant an increased level of systolic and/or diastolic blood pressure. For example, a subject with hypertension can have a systolic blood pressure that is $\geq 120$ mmHg (e.g., $\geq 140$ mmHg or $\geq 160$ mmHg) and/or a diastolic blood pressure that is $\geq 80$ mmHg (e.g., $\geq 90$ mmHg or $\geq 100$ mmHg).

By the term "healthy subject" is meant a subject that does not have a disease (e.g., cardiovascular disease or pulmonary disease). For example, a healthy subject has not been diagnosed as having a disease and is not presenting with one or more (e.g., two, three, four, or five) symptoms of a disease state.

By "risk of death" is meant the risk of death in a subject from a disease or complications associated with a disease compared to a reference population (e.g., a healthy control population). The term risk of death as used herein excludes intentional or accidental death, e.g., death by blunt or crushing trauma, such as a car accident.

Unless otherwise defined, all technical and scientific terms used herein have the same meaning as commonly understood by one of ordinary skill in the art to which this invention belongs. Methods and materials are described herein for use in the present invention. Other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 7A shows SPR analysis of antibody 9F8 (L1). FIG. 7B shows SPR analysis of antibody 7E4 (L2). FIG. 7C shows SPR analysis of antibody 11A7 (L3). FIG. 7D shows SPR analysis of antibody D066 (L4). FIG. 7E shows SPR analysis of antibody D067 (L5). FIG. 7F shows SPR analysis of an irrelevant antibody (L6).

FIG. 8A shows SPR analysis of antibody 9F8 (L1). FIG. 8B shows the SPR analysis of antibody 7E4 (L2). FIG. 8C shows SPR analysis of antibody 11A7 (L3). FIG. 8D shows SPR analysis of antibody 15D6 (L4). FIG. 8E shows SPR analysis of antibody D066 (L5). FIG. 8F shows SPR analysis of antibody D067 (L6).

DETAILED DESCRIPTION

Figure 1:
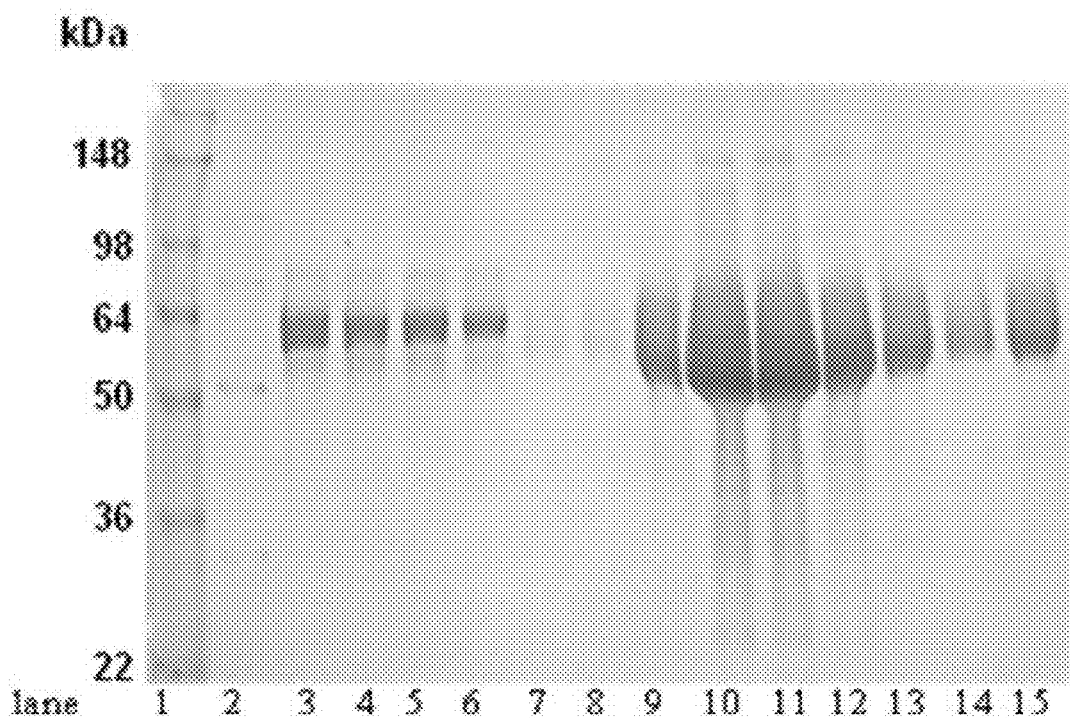
FIG. 1 is an image showing the results of SDS-PAGE gel analysis of fractions from the recombinant human soluble ST2 protein purification. Lanes (10 μL per sample lane) are as follows: 1—MWM (5 μL); 2—His ladder (3 μL); 3—untransfected negative control; 4—supernatant before purification; 5—column flow through; 6—binding buffer wash 1; 7—5 mM wash 2; 8—5 mM wash 3; 9—200 mM eluate fraction 2; 10—200 mM eluate fraction 3; 11—200 mM eluate fraction 4; 12—200 mM eluate fraction 5; 13—200 mM eluate fraction 6; 14—200 mM eluate fraction 7; and 15—0.3 μg soluble ST2.
Figure 2:
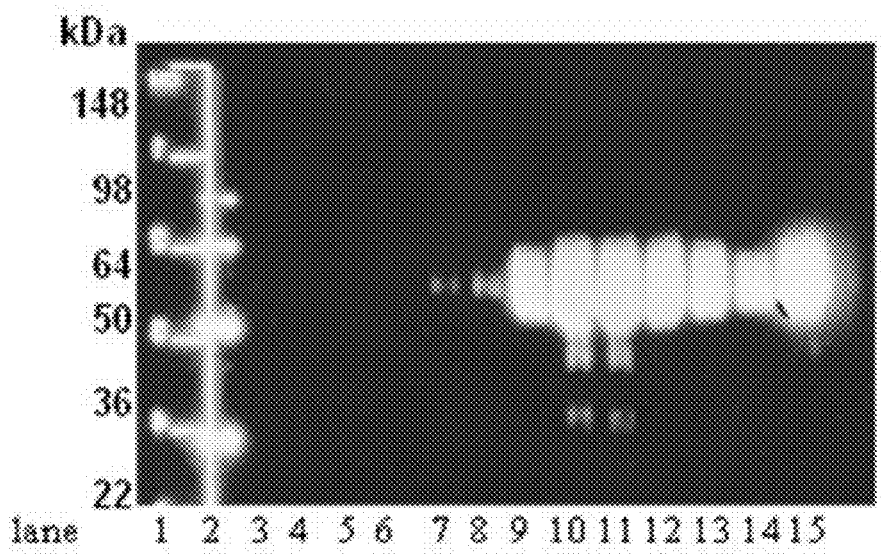
FIG. 2 shows a Western blot of purification fractions detecting the histidine tag in the recombinant human soluble ST2 protein. Lanes (10 μL per lane) are as follows: 1—MWM (5 μL); 2—His ladder (3 μL); 3—supernatant before purification; 4—column flow through; 5—binding buffer wash 1; 6—binding buffer wash 2; 7—5 mM wash 2; 8—5 mM wash 3; 9—200 mM eluate fraction 2; 10—200 mM eluate fraction 3; 11—200 mM eluate fraction 4; 12—200 mM eluate fraction 5; 13—200 mM eluate fraction 6; 14—200 mM eluate fraction 7; and 15—0.3 μg soluble ST2.
Figure 3A:
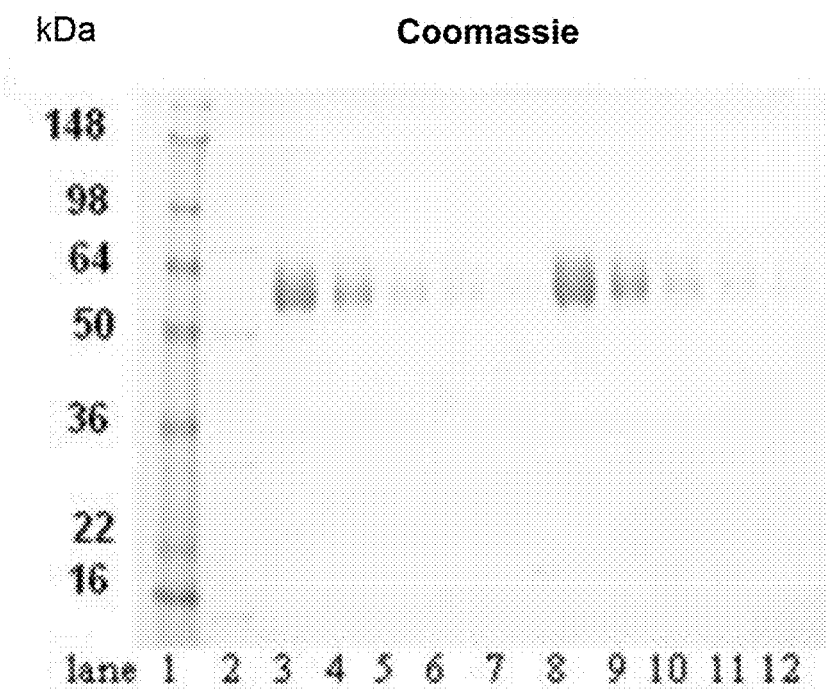
FIGS. 3A-3C show a Coomassie gel (FIG. 3A) and two Western blots of purified recombinant soluble ST2 comparing anti-ST2 commercial antibody D066 (MBL International) (FIG. 3B) with the hexa-histidine antibody (FIG. 3C). Lanes (10 μL/sample lane) are as follows: 1—MWM; 2—His ladder; 3—Serum ST2-His 1000 ng; 4—Serum ST2-His 500 ng; 5—Serum ST2-His 200 ng; 6—Serum ST2-His 100 ng; 7—Serum ST2-His 50 ng; 8—Serum-free ST2-His 1000 ng; 9—Serum-free ST2-His 500 ng; 10—Serum-free ST2-His 200 ng; 11—Serum-free ST2-His 100 ng; and 12—Serum-free ST2-His 50 ng.
Figure 3B:
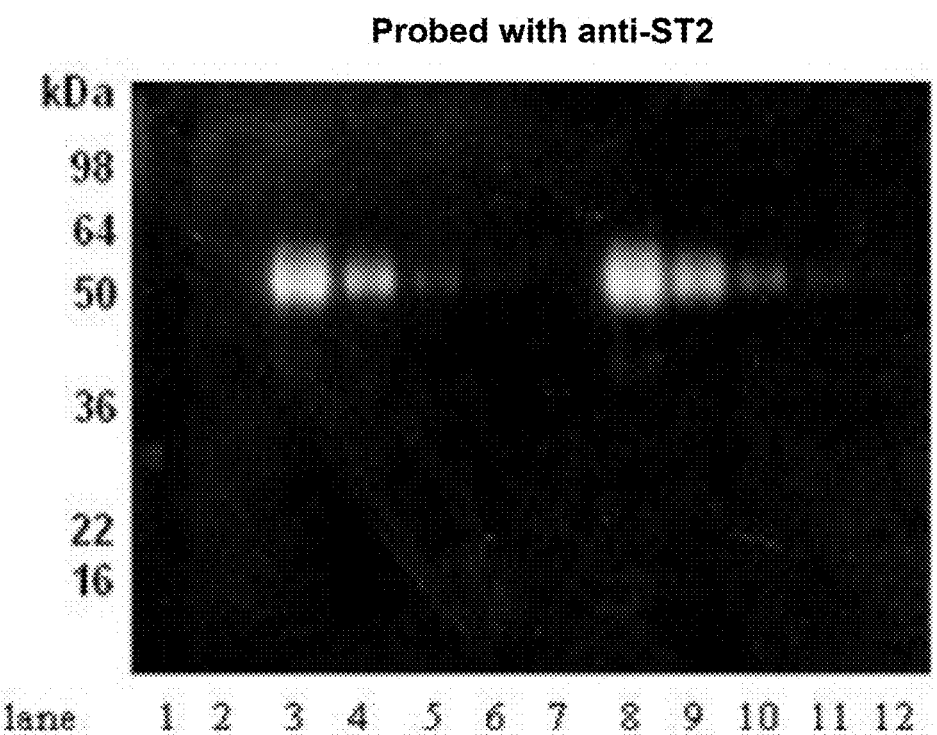
Figure 3C:
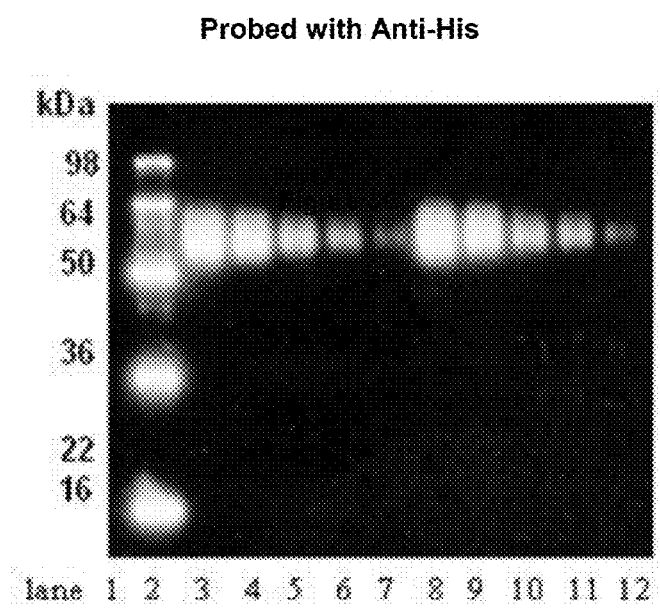

Described herein are antibodies and antigen-binding fragments thereof that specifically bind to human soluble ST2, kits containing these antibodies and fragments, and methods of using these antibodies and fragments.

ST2

The ST2 gene is a member of the interleukin-1 receptor family whose protein product exists both as a trans-membrane form as well as a soluble receptor that is detectable in serum (Kieser et al., *FEBS Lett.* 372(2-3):189-193, 1995; Kumar et al., *J. Biol. Chem.* 270(46):27905-27913, 1995; Yanagisawa et al., *FEBS Lett.* 302(1):51-53, 1992; Kuroiwa et al., *Hybridoma* 19(2):151-159, 2000). Soluble ST2 was described to be markedly up-regulated in an experimental model of heart failure (Weinberg et al., *Circulation* 106(23):2961-2966, 2002), and data suggest that human soluble ST2 concentrations are also elevated in those with chronic severe heart failure (Weinberg et al., *Circulation* 107(5):721-726, 2003), as well as in those with acute myocardial infarction (Shimpo et al., *Circulation* 109(18):2186-2190, 2004).

Without wishing to be bound by theory, the transmembrane form of ST2 is thought to play a role in modulating responses of T helper type 2 cells (Lohning et al., *Proc. Natl. Acad. Sci. U.S.A.* 95(12):6930-6935, 1998; Schmitz et al., *Immunity* 23(5):479-490, 2005), and may play a role in development of tolerance in states of severe or chronic inflammation (Brint et al., *Nat. Immunol.* 5(4):373-379, 2004), while the soluble form of ST2 is up-regulated in growth stimulated fibroblasts (Yanagisawa et al., 1992, supra). Experimental data suggest that the ST2 gene is markedly up-regulated in states of cardiomyocyte stretch (Weinberg et al., 2002, supra) in a manner analogous to the induction of the BNP gene (Bruneau et al., *Cardiovasc. Res.* 28(10):1519-1525, 1994).

Tominaga et al. (*FEBS Lett.* 258:301-304, 1989) isolated murine genes that were specifically expressed by growth stimulation in BALB/c-3T3 cells. Haga et al. (*Eur. J. Biochem.* 270:163-170, 2003) describes that the ST2 gene was named on the basis of its induction by growth stimulation. The ST2 gene encodes two protein products: ST2 or sST2 which is a soluble secreted form, and ST2L, a transmembrane receptor form that is very similar to the interleukin-1 receptors. The HUGO Nomenclature Committee designated the human homolog of ST2, the cloning of which was described in Tominaga et al., *Biochim. Biophys. Acta.* 1171:215-218, 1992, as Interleukin 1 Receptor-Like 1 (IL1RL1). The two terms are used interchangeably herein.

The mRNA sequence of the shorter, soluble isoform of human ST2 can be found at GenBank Acc. No. NM_003856.2 (SEQ ID NO: 2), and the polypeptide sequence is at GenBank Acc. No. NP_003847.2 (SEQ ID NO: 1). The mRNA sequence for the longer form of human ST2 is at GenBank Acc. No. NM_016232.4 (SEQ ID NO: 4), and the polypeptide sequence is at GenBank Acc. No. NP_057316.3 (SEQ ID NO: 3). Additional information is available in the public databases at GeneID: 9173, MIM ID # 601203, and UniGene No. Hs.66. In general, in the methods described herein, the human soluble form of ST2 polypeptide is measured.

Antibodies and Antigen-Binding Antibody Fragments

Provided herein are isolated antibodies and antigen-binding fragments thereof that bind human soluble ST2. The provided antibodies and fragments thereof can bind competitively with an antibody produced by the hybridoma deposited at the ATCC and designated by the Patent Deposit Designation PTA-10431 or PTA-10432 (corresponding to the 7E4 and the 9F8 antibodies, respectively). In some embodiments, the antibody or fragment does not bind competitively with D066-3 and D067-3 antibody (MBL International) (described in U.S. Pat. No. 7,087,396), and has a $K_D$ for binding to human soluble ST2 equal to or less than $1.51 \times 10^{-9}$ M. In some embodiments, the antibody or fragment has a $K_D$ for binding to human soluble ST2 equal to or less than $8.59 \times 10^{-10}$ M. Methods for determining the affinity ($K_D$) of an antibody or fragment for binding to human soluble ST2 are described herein (e.g., surface plasmon reasonance) and additional methods are known in the art. Also provided are the 7E4 and 9F8 monoclonal antibodies, produced by the methods described herein, and antigen-binding fragments thereof.

As used herein, the phrase "binds competitively" refers to the situation whereby binding of one antibody or antibody fragment to a given antigen decreases binding of a second antibody or antibody fragment to that same antigen. In some embodiments, an antibody or fragment binds competitively with another antibody or fragment when the two antibodies or fragments bind substantially the same epitope present on a given antigen (e.g., human soluble human ST2). As is shown in more detail in the Examples below, each of the antibodies produced by the hybridomas designated by Patent Deposit Designations PTA-10431 and PTA-10432 recognizes an epitope that is different from various other antibodies that were tested (e.g., D066-3 and D067-3 antibodies from MBL International), and thus does not bind competitively with those test antibodies. In some embodiments, an antibody or fragment descirbed herein binds an epitope on human soluble ST2 that is recognized by an antibody produced by the hybridoma designated by Patent Deposit Designation PTA-10431 or PTA-10432. Methods for determining whether two different antibodies or fragments bind competitively are described herein and art known in the art (e.g., competitive enzymelinked immunosorbent assays).

In some embodiments, the antibodies or fragments bind or show improved binding to an epitope present in recombinant human soluble ST2 protein that is produced from a human cell (e.g., a human fibroblast, epithelial, endothelial, or neuronal cell, an embryonic or adult cell, or a human embryonic kidney cell, e.g., HEK293) that is not present in a recombinant human soluble ST2 produced in a non-human cell type. In some embodiments, the antibodies or fragments bind or show improved binding to an epitope present in a fully glycosylated human soluble ST2 protein (e.g., a human soluble ST2 protein isolated from human cells) that is not present in a recombinant human soluble ST2 protein that is not glycosylated or is mis- or under-glycosylated (e.g., is not fully glycosylated or is glycosylated in a pattern (e.g., number, position, and/or type of sugar(s)) that is not present in the native human soluble ST2 present in a human, e.g., in human serum). In some embodiments, the antibodies and antibody fragments bind to native human soluble ST2 better (e.g., with increased affinity) relative to other commercial available antibodies.

In some embodiments, the antibody is a monoclonal antibody produced by the hybridoma deposited at the ATCC and designated by Patent Deposit Designation PTA-10431 (the 7E4 antibody), or is an antigen-binding fragment of the antibody produced by the hybridoma deposited at the ATTC and designated by the Patent Deposit Designation PTA-10431 (fragments of the 7E4 antibody). In some embodiments, the antibody is a monoclonal antibody produced by the hybridoma deposited at the ATCC and designated by Patent Deposit Designation PTA-10432 (the 9F8 antibody), or is an antigen-binding fragment of the antibody produced by the hybridoma deposited at the ATCC and designated by the Patent Deposit Designation PTA-10432 (fragments of the 9F8 antibody). Combinations of two or more of the antibodies or fragments described herein (e.g., two or more of a 7E4 antibody, 7E4 antibody fragments, 9F8 antibody, and 9F8 antibody fragments) are useful in any of the methods described herein.

The human soluble ST2-binding monoclonal antibodies produced by the hybridomas designated by Patent Deposit Designation PTA-10431 and Patent Deposit Designation PTA-10432 were each generated by immunizing a non-human mammal with a recombinant human soluble ST2 isolated from human embryonic kidney (HEK)-293 cells. Human soluble ST2 has a significant amount/number of post-translational modifications. Based on its amino acid sequence, human soluble ST2 has a predicted molecular weight of about 36 kDa. However, the native protein has a molecular weight of about 58 kDa, due to the presence of post-translation modifications. As is known in the art, such post-translational modifications can have an effect on the ability of an antibody or antibody fragment to bind a given protein. Thus, as described in more detail in the Examples section below, the human soluble ST2-binding monoclonal antibodies produced by the hybridomas designated by Patent Deposit Designation PTA-10431 has a higher affinity for native human soluble ST2 than do other antibodies, and therefore is useful as diagnostic and other reagents.

In some embodiments, an antibody or fragment described herein comprises the heavy and/or light chain (or a fragment thereof) of the antibody produced by the hybridoma designated by Patent Deposit Designation PTA-10431 and/or PTA-10432. In some embodiments, an antibody or fragment described herein comprises the heavy and/or light chain variable region (or a fragment thereof) of the antibody produced by the hybridoma designated by Patent Deposit Designation PTA-10431 and/or PTA-10432.

As is known in the art, an antibody's specificity towards a given antigen is mediated by the heavy and light chain variable regions. In particular, the specificity of an antibody towards a given antigen is primarily determined by short sequences within the heavy and light chain variable regions called complementarity determining regions, or CDRs. In some embodiments, an antibody or fragment described herein contains one or more (e.g., one, two, three, four, five, or six) CDRs of the light and/or heavy chain of the antibody produced by the hybridoma designated by Patent Deposit Designation PTA-10431 and/or PTA-10432. In some embodiments, an antibody or fragment described herein comprises each of the CDRs of the heavy chain of the antibody produced by the hybridoma designated by Patent Deposit Designation PTA-10431 or PTA-10432. In some embodiments, an antibody or fragment described herein comprises each of the CDRs of the light chain of the antibody produced by the hybridoma designated by Patent Deposit Designation PTA-10431 or PTA-10432. In some embodiments, an antibody or fragment described herein comprises each of the CDRs of the antibody (all of the heavy and light chain CDRs) produced by the hybridoma designated by Patent Deposit Designation PTA-10431 or PTA-10432.

Also provided are isolated antibodies and antigen-binding antibody fragments that specifically bind to human soluble ST2 that are produced by a process that includes immunizing a non-human mammal with a recombinant human soluble ST2 isolated from a kidney cell (e.g., a human kidney cell, an embryonic kidney cell, and a human embryonic kidney cell). In some embodiments, the recombinant human soluble ST2 is fully glycosylated or contains all the post-translational modifications present in the native soluble ST2 protein.

In some embodiments, an antibody or fragment described herein is chimeric in that it comprises at least one human constant region. For example, the constant regions of the antibodies produced by the hybridoma designated by Patent Deposit Designation PTA-10431 or PTA-10432 can be replaced with a human constant region. Chimeric antibodies are typically less immunogenic to humans, relative to non-chimeric antibodies, and thus offer therapeutic benefits in certain situations. In some embodiments, a chimeric antibody described herein comprises an IgG1 constant region. Those skilled in the art will be aware of a variety of human constant regions. Methods for making chimeric antibodies are known in the art.

In some embodiments, an antibody or fragment described herein is humanized in that it comprises at least one human framework region. For example, one or more (e.g., one, two, three, four, five, or six) framework regions of the antibodies produced by the hybridoma designated by Patent Deposit Designation PTA-10431 or PTA-10432, can be replaced with one or more (e.g., one, two, three, four, five, or six) human framework regions. Humanized antibodies are typically less immunogenic to humans, relative to non-humanized antibodies, and thus offer therapeutic benefits in certain situations. Those skilled in the art will be aware of a variety of human framework regions. Methods for producing humanized antibodies are known in the art.

For example, CDR homology-based methods can be used for humanization (see, e.g., Hwang et al., *Methods* 36:35, 2005). These methods generally involve substitution of non-human CDRs into a human variable domain framework based on similarly structured non-human and human CDRs, rather than similarly structured non-human and human frameworks. The similarity of the non-human and human CDRs is generally determined by identifying human genes of the same chain type (light or heavy) that have the same combination of canonical CDR structures as the non-human (e.g., mouse) binding molecules and thus retain three-dimensional conformation of CDR peptide backbones. Secondly, for each of the candidate variable genes with matching canonical structures, residue to residue homology between the non-human and candidate human CDRs is evaluated. Finally, to generate a humanized binding molecule, CDR residues of the chosen human candidate CDR not already identical to the non-human CDR are converted to the non-human (e.g., mouse) sequence. In some embodiments, no mutations of the human framework are introduced into the humanized binding molecule.

In some embodiments, the substitution of non-human CDRs into a human variable domain framework is based on the retention of the correct spatial orientation of the non-human variable domain framework by identifying human variable domain frameworks that will retain the same conformation as the non-human variable domain frameworks from which the CDRs were derived. In some embodiments, this is achieved by obtaining the human variable domains from human binding molecules whose framework sequences exhibit a high degree of sequence identity with the non-human variable framework domains from which the CDRs were derived. See, for example, Kettleborough et al., *Protein Engineering* 4:773, 1991; Kolbinger et al., *Protein Engineering* 6:971, 1993; and WO 92/22653.

In some embodiments, an antibody or fragment described herein is monospecific in that it recognizes only a single epitope. Monospecific antibodies are known in the art (see, for example, WO/9639858). In some embodiments, an antibody or fragment described herein is bispecific in that it recognizes more than one epitope (e.g., two epitopes). Bispecific antibodies are known in the art (see, for example, U.S. Patent Application Publication No. 2009/0162360). In some embodiments, monospecific or bispecific antibodies or fragments described herein bind the epitope recognized by an antibody or antibody fragment having the CDRs of the monoclonal antibody produced by the hybridoma designated by Patent Deposit Designation PTA-10431 or PTA-10432. In some embodiments, a bispecific antibody or fragment binds human soluble ST2, as well as a different non-ST2 polypeptide. In some embodiments, a bispecific antibody or fragment binds two different epitopes of human soluble ST2. In some embodiments, an antibody or fragment described herein is divalent (see, for example, WO/1999/064460). For a further description of other types of antibodies and fragments that can include one or more of the CDRs of the monoclonal antibodies produced by the hybridomas designated by Patent Deposit Designation PTA-10431 or PTA-10432, see US Patent Application Publication No. 20070105199 and WO/2007/059782.

In some embodiments, a fragment (e.g., an antigen-binding fragment) is derived from a whole antibody molecule, e.g., a monoclonal antibody. The antibody can be, for example, cleaved on the carboxy-terminal side of its hinge region (e.g., with pepsin) to generate a F(ab')$_2$ fragment, or on the amino-terminal side of its hinge region (e.g., with papain) to generate Fab fragments. In some embodiments, an antigen-binding fragment described herein is a Fab fragment, a F(ab')$_2$ fragment, a scFv fragment, a linear antibody, a multispecific antibody fragment such as a bi-specific, a tri-specific, or a multi-specific antibody (e.g., a diabody, a triabody, or a tetrabody), a minibody, a chelating recombinant antibody, an intrabody, a nanobody, a small modular immunopharmaceutical (SMIP), a binding-domain immunoglobulin fusion protein, a camelid antibody, or a V$_{HH}$ containing antibody. Methods for producing these fragments are known in the art.

In some embodiments, a human soluble ST2-binding antibody or an antigen-binding antibody fragment described herein contains a polypeptide having one or more amino acid substitutions, deletions, or insertions as compared to the heavy and/or light chain of the antibody produced by the hybridoma designated by Patent Deposit Designation PTA-10431 or PTA-10432. Substitutions, deletions, or insertions can be introduced by standard techniques, such as site-directed mutagenesis or PCR-mediated mutagenesis, of a nucleic acid molecule encoding a polypeptide comprising the heavy and/or light chain of the antibody produced by the hybridoma designated by Patent Deposit Designation PTA-10431 or PTA-10432 (e.g., or a nucleic acid encoding one or more (e.g., one, two, or three) of the CDR regions of the heavy or light chain). In some embodiments, conservative amino acid substitutions are made at one or more positions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan; histidine). Thus, an amino acid residue in a polypeptide of an anti-human soluble ST2 antibody or a human soluble ST2-binding antibody fragment can be replaced with another amino acid residue from the same side chain family.

In some embodiments, a human soluble ST2-binding antibody or a human soluble ST2-binding antibody fragment described herein comprises an amino acid sequence that is at least 90% identical, at least 95%, 96%, 97%, 98%, 99%, or 100% identical to the heavy and/or light chain of the antibody produced by the hybridoma designated by Patent Deposit Designation PTA-10431 or PTA-10432 (e.g., or at least 90%, 95%, 96%, 97%, 98%, 99%, or 100% identical to at least one (e.g., one, two, or three) CDR of the heavy or light chain of the antibody producted by the hybridoma designated by Patent Deposit Designation PTA-10431 or PTA-10432). For example, a human soluble ST2-binding antibody or a human soluble ST2-binding antibody fragment described herein may contain one or more CDRs that contain one or more amino acid substitutions, deletions, or insertions in the corresponding CDR sequence found in a heavy or light chain of the antibody produced by the hybridoma designated by Patent Deposit Designation PTA-10431 or PTA-10432.

In some embodiments, compositions described herein contain two or more different human soluble ST2-binding antibodies or human soluble ST2-binding antibody fragments described herein. For example, a composition described herein can contain antibodies produced by each of the hybridomas designated by Patent Deposit Designation PTA-10431 and PTA-10432. As described in more detail in the Examples section below, such a combination of antibodies exhibits increased affinity for the ST2 antigen as compared to either antibody individually, and as compared to other commercially available antibodies. Such compositions containing the antibodies or antigen-binding fragments described herein will be useful in a variety of methods, e.g., diagnostic methods. In some embodiments, the compositions described herein contain two or more different ST2-binding fragments (e.g., Fab fragments, F(ab)$_2$ fragments, or scFv fragments), such as fragments derived from antibodies produced by the hybridomas designated by Patent Deposit Designation PTA-10431 or PTA-10432.

In any of the above methods, the antibody or antibody fragment can be glycosylated or labeled. For example, antibodies and antibody fragments can be labeled with a detectable substance including, but not limited to, various enzymes, prosthetic groups, fluorescent materials, luminescent materials, bioluminescent materials, and radioactive materials. Examples of suitable enzymes include horseradish peroxidase, alkaline phosphatase, f3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, quantum dots, or phycoerythrin; an example of a luminescent material includes luminol; examples of bioluminescent materials include luciferase, luciferin, and aequorin, and examples of suitable radioactive material include $^{125}I$, $^{131}I$, $^{35}S$, or $^3H$.

Hybridomas

Also provided herein are novel hybridomas that produce antibodies that bind human soluble ST2. As is known the art, the term "hybridoma" refers to a cell that is produced by the fusion of an antibody-producing lymphocyte and a non-antibody-producing cancer cell, usually a myeloma or lymphoma. After fusion, hybridomas proliferate and produce the specific monoclonal antibody that was originally produced by the fused lymphocyte. In some embodiments, the hybridoma provided is a hybridoma deposited at the ATCC and designated by Patent Deposit Designation PTA-10431 or PTA-10432. In some embodiments, individual cells, harvested cells, and cultures containing cells that are derived from the hybridoma deposited at the ATCC and designated by Patent Deposit Designation PTA-10431 or PTA-10432 are also provided.

Methods of Using the Provided Antibodies and Fragments

One or more of any of the antibodies or antibody fragments described herein can be used in methods for quantitating a level of human soluble ST2 in a sample, e.g., a sample from a subject, especially for predicting the risk of death within a year, determining whether to discharge or to initiate or continue treatment of a subject on an impatient basis, selecting a subject for participation in a clinical study, diagnosing a subject as having a disease, or identifying a subject at risk of developing a disease.

Methods of Quantitating a Level of Human Soluble ST2

Provided herein are methods for determining a level of human soluble ST2 in a sample from a subject including contacting the sample with at least one antibody or antibody fragment described herein; and detecting the binding of the antibody or fragment to human soluble ST2. In some embodiments, at least two (e.g., two, three, or four) antibodies or antibody fragment described herein are used to determine a level of human soluble ST2 in a sample from a subject. In some embodiments, the subject is undiagnosed or is not presenting with one or more (e.g., two, three, or four) symptoms of a disease. In some embodiments, the subject has been diagnosed as having a disease associated with elevated levels of ST2 (e.g., heart failure, coronary artery disease, cardiovascular disease, acute coronary syndrome, renal insufficiency, stroke, or any of the other diseases described herein). In some embodiments, the subject has one or more (e.g., two, three, or four) of: hypertriglyceridemia, hypercholesterolemia, hypertension, renal insufficiency, and a body mass index of $\geq 30$. In some embodiments, the sample contains blood, serum, or plasma.

In some embodiments, the sample can be collected from the subject by a health care professional (e.g., a phlebotomist, a physician, a nurse, a physician's assistant, or a laboratory technician). The sample can be stored (e.g., at ≦4° C., ≦0° C., or −80° C.) for a period of time before the sample is contacted with at least one antibody or fragment described herein, and the binding of the antibody or fragment is detected. Methods for contacting a biological sample with an antibody or antibody fragment and detecting the binding of the antibody or fragment are described herein and additional methods are known in the art. The quantitation can also include control experiments for detecting the binding of the at least one antibody or antibody fragment described herein to a recombinant purified human soluble ST2 (e.g., a recombinant human soluble ST2 isolated from human embryonic kidney cells).

In some embodiments, the level of human soluble ST2 in a normal or healthy subject is quantitated. A normal or healthy subject is a subject that does not suffer from an ST2-associated condition (e.g., a ST2-associated condition as described herein), is undiagnosed as having a disease (e.g., any of the diseases described herein), and does not present with two or more (e.g., two, three, or four) symptoms of a disease. Normal or healthy subjects can be confirmed by any of a variety of techniques known in the art, including without limitation, by biomarker screening or physical examination (e.g., by external manifestation of the absence of two or more symptoms associated with an ST2-associated condition or any other disease described herein). For example, normal or healthy subjects can be screened for the absence of occult CVD or inflammatory disease by screening for low levels of one or more markers including, but not limited to, brain natriuretic peptide (BNP), procalcitonin (PCT), C-reactive protein (CRP), and interleukin-6 (IL-6). Those skilled in the art will be aware of other suitable markers for determining that a normal or healthy subject does not exhibit occult CVD or inflammatory disease, or any of the other diseases described herein.

Quantitation of human soluble ST2 levels in a sample from a subject (e.g., a normal or healthy subject) is useful in a variety of circumstances. In some embodiments, human soluble ST2 levels of subjects (e.g., normal or healthy subjects, subjects having an increased risk of developing a disease, subjects diagnosed with disease, or subjects presenting with two or more symptoms of a disease) can be quantitated at periodic intervals, e.g., daily, weekly, biweekly, monthly, bimonthly, annually, etc., or at a periodic physical examination. Any of a variety of techniques known to those skilled in the art, including those described herein, can be used to quantitate human soluble ST2 levels in a subject using the antibodies and antigen-binding fragments of antibodies described herein.

In some embodiments, the level of human soluble ST2 in a control subject (e.g., a normal or healthy subject) is quantitated to arrive at a reference level for use in determining that a subject does not have an ST2-associated condition, is at risk of developing a disease, or is at risk of death within one year. For example, human soluble ST2 levels in a subject that does not suffer from a disease, such as, without limitation, a cardiovascular disease, heart failure, coronary artery disease, acute coronary syndrome, renal insufficiency, stroke, a pulmonary disease, sepsis, Kawasaki disease, or a Th2-associated disease, or any other disease described herein, can be quantitated to arrive at a human soluble ST2 reference level.

In some embodiments, at least one of any of the antibodies or antigen-binding fragments disclosed herein can be used in quantitating human soluble ST2 levels in a subject (e.g., a normal or healthy subject). For example, human soluble ST2 levels in a subject (e.g., a normal or healthy subject) can be quantitated in immunoassays using at least one of any antibody or antigen-binding fragment described herein (e.g., an antibody or fragment that binds competitively with an antibody produced a hybridoma deposited at the ATCC and is designated by Patent Deposit Designation PTA-10431 or PTA-104312, or both).

In some embodiments, the level of human soluble ST2 in a sample is quantitated to ensure reproducibility of routine performance, reference ranges, clinical cutoffs, and the like. For example, the levels of human soluble ST2 in two or more samples, e.g., reference samples, can be quantitated and the coefficient of variation ("CV") between the human soluble ST2 levels of the two or more samples can be assessed. Additionally or alternatively, the level of human soluble ST2 in the sample (or subject) can be quantitated two or more separate times (e.g., using different batches of a reference sample, or different samples taken from the same subject), and the CV between the human soluble ST2 levels can be determined. In some embodiments, the CV between human soluble ST2 levels is less than 20%, e.g., less than 19%, 18%, 17%, 16%, 15%, 14%, 13%, 12% 11%, 10%, 9%, 8%, 7%, 6%, 5%, 4%, 3%, 2%, 1%, or less.

In some embodiments, methods are provided for determining whether a subject has a normal human soluble ST2 level. Determining whether a subject has a normal human soluble ST2 level is useful in a variety of circumstances. In some embodiments, methods for determining whether a subject has a normal human soluble ST2 level comprise assaying the level of human soluble ST2 in a sample from the subject (e.g., any of the samples described above such as, without limitation, samples containing blood, serum, or plasma), wherein the subject is determined to have a normal human soluble ST2 level if the level of human soluble ST2 in the sample is found to be substantially similar to the known normal or median human soluble ST2 level, or if the level of human soluble ST2 in the sample falls within a certain range, e.g., around a known normal or median human soluble ST2 level (e.g., the 95% confidence interval or the interquartile range, or any of the ranges listed in Table 9). For example, a subject can be determined to have a normal human soluble ST2 level if a sample from the subject is assayed, and the level of human soluble ST2 in the sample is found to be within the 95% confidence interval around a known normal or median human soluble ST2 level, e.g., a median level in a normal or healthy subject. Additionally or alternatively, a subject can be determined to have a normal human soluble ST2 level if a sample from the subject is assayed, and the level of human soluble ST2 in the sample is found to be within the interquartile range around a known normal or median human soluble ST2 level.

In some embodiments, a subject is determined to have a normal human soluble ST2 level if the human soluble ST2 level in a sample from the subject is about 18.8 ng/mL. In some embodiments, a subject is determined to have a normal human soluble ST2 level if the human soluble ST2 level in a sample is within a range of about 14.5 to about 25.3 ng/mL. In some embodiments, a subject is determined to have a normal human soluble ST2 level if the human soluble ST2 level in a sample is within a range of about 18.1 to about 19.9 ng/mL.

In some embodiments, a female subject is determined to have a normal human soluble ST2 level if the human soluble ST2 level in a sample from the subject is about 16.2 ng/mL. In some embodiments, a female is determined to have a normal human soluble ST2 level if the human soluble ST2 level in a sample is within any of the ranges listed in Table 9.

In some embodiments, a male subject is determined to have a normal human soluble ST2 level if the human soluble ST2 level in a sample from the subject is about 23.6 ng/mL. In some embodiments, a male is determined to have a normal human soluble ST2 level if the human soluble ST2 level in a sample is within any of the ranges listed in Table 9.

In some embodiments, the subject (e.g., male or female subject) is determined to have a normal soluble ST2 level if the human soluble ST2 level in a sample from the subject is below a threshold (e.g., 25.3 ng/mL, or 19.9 ng/mL (for females) or 30.6 ng/mL (for males)).

The term "about" or "substantially the same" as used in reference to a value or range of human soluble ST2 levels (e.g., a range of normal human soluble ST2 levels) in a subject refers to an interval around the reference value or range, e.g., a value or range that one of skill in the art would consider equivalent to the reference value or range (e.g., any of the ranges listed in Table 9) for the purpose of assessing human soluble ST2 levels (e.g., normal human soluble ST2 levels or human soluble ST2 levels in a group of patients having a disease or presenting with two or more disease symptoms). As used herein, a value or range of human soluble ST2 levels (e.g., normal human soluble ST2 levels) is "about" a reference value or range when it is within +/−25% of the reference value or range, e.g., +/−20%, +/−15%, +/−10%, +/−9%, +/−8%, +/−7%, +/−6%, +/−5%, +/−4%, +/−3%, +/−2%, or +/−1% of the value or range.

In some embodiments, at least one or two of any of the antibodies or antigen-binding fragments described herein can be used in determining whether a subject has a normal human soluble ST2 level, a level of human soluble ST2 that is correlated with a disease, or a level of human soluble ST2 that is correlated with an increased risk of developing a disease or an increased risk of death within one year.

Methods of Predicting the Risk of Mortality within One Year

Also provided are methods of predicting the risk of mortality in a subject within one year that include obtaining a sample from a subject and determining the level of human soluble ST2 in the sample using at least one antibody or antibody fragment described herein. An elevated level or substantially the same level of human soluble ST2 in the sample compared to a reference level of human soluble ST2 indicates that the subject has an increased risk of death within one year (e.g., an increased risk of death within one year compared to subjects (e.g., subjects having or diagnosed with same disease) having a decreased level of human soluble ST2 in the sample compared to the same reference level of ST2). A decreased level of human soluble ST2 in the sample compared to a reference level of human soluble ST2 indicates that the subject has a lower risk of death within one year (e.g., a lower risk of death compared to subjects (e.g., subjects having or diagnosed with the same disease) having an elevated level or substantially the same level of human soluble ST2 in the sample compared to the same reference level of human soluble ST2). The level of risk of death within one year determined by the methods described herein will depend on the disease state.

In some embodiments the subject is undiagnosed or is not presenting with one or more (e.g., two, three, four, or five) symptoms of a disease. In some embodiments, the subject has been diagnosed as having a disease (e.g., heart failure, coronary artery disease, cardiovascular disease, acute coronary syndrome, renal insufficiency, or stroke, or any of the diseases described herein). In some embodiments, the subject has one or more (e.g., one, two, three, or four) of: hypertriglyceridemia, hypercholesterolemia, hypertension, and a body mass index of $\geq 30$. In some embodiments, the determining is performed using at least one (e.g., two, three, four, or five) antibodies or fragments described herein.

In some embodiments, the reference level of human soluble ST2 is a threshold level of human soluble ST2 (e.g., a median level of human soluble ST2 or a percentile (e.g., $75^{th}$, $80^{th}$, $85^{th}$, $90^{th}$, or $95^{th}$ percentile, or any of the ranges or concentrations listed in Table 9) of the median level of human soluble ST2 in a healthy patient population, e.g., a healthy male patient population or a healthy female patient population). In some embodiments, the reference level can be a level of human soluble ST2 present in a sample of a subject not presenting with one or more symptoms of a disease associated with increased levels of ST2. In some embodiments, the reference level can be a level of human soluble ST2 present in a sample of a subject not diagnosed as having a disease (e.g., heart failure, coronary artery disease, cardiovascular disease, acute coronary syndrome, renal insufficiency, stroke, or any of the diseases described herein) or a subject identified as not being at risk of developing a disease (e.g., any of the diseases described herein). Additional reference levels can be determined by those skilled in the art.

In some embodiments, the human soluble ST2 reference level is between about 30 ng/mL to about 35 ng/mL. In some embodiments, where the subject has heart failure, the human soluble ST2 reference level is between about 30 ng/mL to about 35 ng/mL. In some embodiments, the human soluble ST2 reference level is about 35 ng/mL or about 60 ng/mL.

In some embodiments, the sample contains blood, serum, or plasma. The sample can be obtained and the determination of the level of human soluble ST2 using at least one antibody or fragment described herein can be performed as described herein.

Methods of Determining Whether to Discharge or to Initiate or Continue Treatment of a Subject on an Inpatient Basis Also provided are methods of determining whether to discharge or to initiate or continue treatment of a subject on an impatient basis including obtaining a sample from a subject, and determining the level of human soluble ST2 in the sample using at least one (e.g., two) antibody or antibody fragment described herein, where an elevated level of human soluble ST2 in the sample compared to a reference level of human soluble ST2 indicates that inpatient treatment (e.g., hospitalization or admittance into an assisted-care facility) of the subject should be initiated or continued, and a decreased or an equal level of human soluble ST2 in the sample compared to a reference level of human soluble ST2 in the sample indicates that the subject should be discharged. The method can be performed several times for the same subject in order to determine whether inpatient treatment should be continued (e.g., performed once every week, twice a week, three times a week, one a month, twice a month, three times a month, and four times a month).

In some embodiments, the subject is undiagnosed, is not presenting with two or more symptoms of a disease state, or has not been identified as being at risk of developing a disease (e.g., any of the diseases described herein). In some embodiments, the subject has been diagnosed as having a disease (e.g., heart failure, coronary artery disease, cardiovascular disease, acute coronary syndrome, renal insufficiency, or stroke, or any of the diseases described herein), presents with one or more symptoms of a disease (e.g., any of the diseases described herein, or has been identified as being at risk of developing a disease (e.g., any of the diseases described herein). In some embodiments, the subject has one or more (e.g., one, two, three, or four) of: hypertriglyceridemia, hypercholesterolemia, hypertension, and a body mass index of $\geq 30$. In some embodiments, the subject has not been diagnosed as having heart failure, coronary artery disease, cardiovascular disease, acute coronary syndrome, renal insufficiency, or stroke, or any of the diseases described herein. In some embodiments, the determination of the level of human soluble ST2 is performed using at least two antibodies or antibody fragments described herein.

In some embodiments, the reference levels of human soluble ST2 can be any of the reference levels described herein. Additional human soluble ST2 reference levels can be determined by those skilled in the art. In some embodiments, the sample contains blood, serum, or plasma. The sample can be obtained and the determination of the level of human soluble ST2 using at least one antibody or fragment described herein can be performed as described herein.

Methods of Selecting a Subject for Participation in a Clinical Study

Also provided are methods for selecting a subject for participation in a clinical study. These methods include obtaining a sample from a subject, determining the level of human soluble ST2 in the sample using at least one antibody or antibody fragment described herein, and selecting the subject for participation in a clinical study if the subject's level of human soluble ST2 relative to a reference level of human soluble ST2 indicates that the subject should be selected for participation in a clinical study. In some embodiments, the presence of an elevated level of human soluble ST2 indicates that the subject should be selected for participation in a clinical study. In some embodiments, the presence of an elevated level of human soluble ST2 indicates that the subject should be excluded from participation in a clinical study.

In some embodiments, the subject is undiagnosed, is not presenting with one or more symptoms of a disease (e.g., any of the diseases described herein), or has not been identified as being at risk of developing a disease (e.g., any of the diseases described herein). In some embodiments, the subject has been diagnosed as having a disease (e.g., heart failure, coronary artery disease, cardiovascular disease, acute coronary syndrome, renal insufficiency, or stroke, or any of the diseases described herein), presents with one or more symptoms of a disease (e.g., any of the diseases described herein), or has been identified as being at low risk of developing a disease (e.g., any of the diseases described herein). In some embodiments, the subject has one or more (e.g., one, two, three, or four) of: hypertriglyceridemia, hypercholesterolemia, hypertension, and a body mass index of $\geq 30$. In some embodiments, the determining is performed using at least two antibodies or fragments described herein.

In some embodiments, the reference levels of human soluble ST2 can be any of the reference levels described herein. Additional human soluble ST2 reference levels can be determined by those skilled in the art. In some embodiments, the sample contains blood, serum, or plasma. The sample can be obtained and the determination of the level of human soluble ST2 using at least one antibody or fragment described herein can be performed as described above.

Methods of Selecting a Treatment

Also provided are methods of selecting a therapeutic treatment for a subject including obtaining a sample from a subject and determining a level of human soluble ST2 in the sample using at least one of the antibodies and fragments described herein, wherein an elevated level of human soluble ST2 in the sample relative to a reference human soluble ST2 level indicates that the subject should be provided a specific therapeutic treatment. For example, the specific treatment can be selected from the group of: nitrates, calcium channel blockers, diuretics, thrombolytic agents, digitalis, renin-angiotensin-aldosterone system (RAAS) modulating agents (e.g., beta-adrenergic blocking agents (e.g., alprenolol, bucindolol, carteolol, carvedilol, labetalol, nadolol, penbutolol, pindolol, propranolol, sotalol, timolol, cebutolol, atenolol, betaxolol, bisoprolol, celiprolol, esmolol, metoprolol, and nebivolol), angiotensin-converting enzyme inhibitors (e.g., benazepril, captopril, enalapril, fosinopril, lisinopril, moexipril, perindopril, quinapril, ramipril, and trandolapril), aldosterone antagonists (e.g., spironolactone, eplerenone, canrenone (canrenoate potassium), prorenone (prorenoate potassium), and mexrenone (mexrenoate potassium)), renin inhibitors (e.g., aliskiren, remikiren, and enalkiren), and angiotensin II receptor blockers (e.g., valsartan, telmisartan, losartan, irbesartan, and olmesartan)), and cholesterol-lowering agents (e.g., a statin). Additional methods for treatment are also known in the art, e.g., Braunwald's Heart Disease: A Textbook of Cardiovascular Medicine, Single Volume, 9th Edition. The specific treatment can also be the administration of at least one or more new therapeutic agents to the subject, an alteration (e.g., increase or decrease) in the frequency, dosage, or length of administration of one or more therapeutic agents to the subject, or the removal of at least one or more therapeutic agents from the patient's treatment regime. The treatment can also be inpatient care of the subject (e.g., admittance or re-admittance of the subject to a hospital (e.g., an intensive care or critical care unit) or an assisted-care facility). In some embodiments, the treatment is surgery (e.g., organ or tissue transplant or angioplasty).

In some embodiments, the reference levels of human soluble ST2 can be any of the reference levels described herein. Additional human soluble ST2 reference levels can be determined by those skilled in the art. In some embodiments, the sample contains blood, serum, or plasma. The sample can be obtained and the determination of the level of human soluble ST2 using at least one antibody or fragment described herein can be performed as described above.

Methods of Diagnosing a Subject

The methods described herein are useful in a wide variety of clinical contexts. For example, such methods can be used for general population screening, including screening by doctors, e.g., in hospitals and outpatient clinics, as well as the emergency room.

In some embodiments, the methods described herein are useful for determining the likelihood of the presence of a disease in a subject. Increased levels of human soluble ST2 are often associated with the presence of certain diseases such as, without limitation, cardiovascular diseases, pulmonary diseases, sepsis, Kawasaki disease, and Th2-associated diseases, and any of the other diseases described herein.

A Th2-associated disease is a disease associated with an abnormal type-2 T helper cell (Th2) response. A Th2-associated disease is characterized by several factors, including without limitation, the presence of TNF-alpha, IL-4, -5, -6, 10 and -13, but not IFN-gamma (Robinson, *J. Allergy Clin. Immunol.* 92:313, 1993). CD4+ T-cells are classified according to the cytokines that they secrete. Th2 cells secrete large amounts of interleukin-4 (IL-4), IL-5, and IL-13, which promote antibody production by B-cells and collagen synthesis by fibroblasts, whereas Th1 cells secrete large amounts of interferon-y and associated proinflammatory cytokines Th1-type and Th2-type cytokines can cross-regulate each other's responses. An imbalance of Th1/Th2 responses is thought to contribute to the pathogenesis of various infections, allergic responses, and autoimmune diseases. Certain exemplary Th2-associated diseases include, without limitation, systemic lupus erythematosus and asthma, as well as inflammatory conditions that are mainly independent of a Th2 response, such as septic shock or trauma (Trajkovic et al., *Cytokine Growth Factor Rev.* 15:87-95, 2004; Brunner et al., *Intensive Care Med.* 30:1468-1473, 2004). Other exemplary Th2-associated diseases include preeclampsia and multiple sclerosis. In some embodiments, a Th2-associated disease is an autoimmune disease. An autoimmune disease typically results when the subject's immune system is activated against one or more components (cells, tissues, or cell/tissue-free molecules) of the subject and attacks that subject's own normal organs, tissues, or cells. Exemplary autoimmune diseases include, but are not limited to, adrenergic drug resistance, alopecia greata, ankylosing spondylitis, antiphospholipid syndrome, autoimmune Addison's disease, autoimmune diseases of the adrenal gland, allergic encephalomyelitis, autoimmune hemolytic anemia, autoimmune hepatitis, autoimmune inflammatory eye disease, autoimmune neonatal thrombocytopenia, autoimmune neutropenia, autoimmune oophoritis and orchitis, autoimmune thrombocytopenia, autoimmune thyroiditis, Behcet's disease, bullous pemphigoid, cardiomyopathy, cardiotomy syndrome, celiac sprue-dermatitis, chronic active hepatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, dense deposit disease, diseases associated with effects from organ transplantation, discoid lupus, essential mixed cryoglobulinemia, fibromyalgia-fibromyositis, glomerulonephritis (e.g., IgA nephrophathy), gluten-sensitive enteropathy, Goodpasture's syndrome, graft vs. host disease (GVHD), Graves' disease (including e.g., Graves thyroiditis and Graves opthalmopathy), Guillain-Barre, hyperthyroidism (i.e., Hashimoto's thyroiditis), idiopathic pulmonary fibrosis, idiopathic Addison's disease, idiopathic thrombocytopenia purpura (ITP), IgA neuropathy, Insulin Resistance Syndrome, juvenile arthritis, lichen planus, lupus erythematosus, Meniere's disease, Metabolic Syndrome, mixed connective tissue disease, multiple sclerosis, Myasthenia Gravis, myocarditis, diabetes (e.g., Type I diabetes or Type II diabetes), neuritis, other endocrine gland failure, pemphigus vulgaris, pernicious anemia, polyarteritis nodosa, polychrondritis, Polyendocrinopathies, polyglandular syndromes, polymyalgia rheumatica, polymyositis and dermatomyositis, postmyocardial infarction, primary agammaglobulinemia, primary biliary cirrhosis, psoriasis, psoriatic arthritis, Raynaud's phenomenon, relapsing polychondritis, Reiter's syndrome, rheumatic heart disease, rheumatoid arthritis, sarcoidosis, scleroderma, Sjogren's syndrome, stiff-man syndrome, systemic lupus erythematosus, Takayasu arteritis, temporal arteritis/giant cell arteritis, ulcerative colitis, urticaria, uveitis, uveitis opthalmia, vasculitides, such as dermatitis herpetiformis vasculitis, vitiligo, and Wegener's granulomatosis.

A cardiovascular disease is a disorder of the heart and blood vessels, and includes disorders of the arteries, veins, arterioles, venules, and capillaries. Cardiovascular diseases diagnosed by a method described herein can include, without limitation, congestive heart failure (HF), acute coronary artery disease (CAD), arrhythmia, asymmetric septal hypertrophy (e.g., left ventricular hypertrophy with resultant diastolic dysfunction), cardiomyopathy, valvular dysfunction, pericarditis, atherosclerosis, and acute myocardial infarction (MI).

A pulmonary disease is a disorder of the lungs. Pulmonary diseases diagnosed by methods described herein can include, without limitation, chronic obstructive pulmonary disease (COPD), asthma, pneumonia, pneumothorax, pulmonary embolism, advanced respiratory distress syndrome (ARDS), pleural effusion, metastatic disease, pulmonary edema, gastrooesophageal reflux disease with aspiration, interstitial fibrosis, pneumoconiosis, granulomatous disease, collagen vascular disease, and restrictive lung disease.

If the subject has an elevated level of human soluble ST2, e.g., as compared to a reference level, a decision to treat the subject aggressively can be made, and the subject can be, e.g., admitted to a hospital for treatment as an inpatient, e.g., in a hospital (e.g., an acute or critical care department) or assisted-care facility. Determining whether a subject has a disease such as cardiovascular disease, or pulmonary disease, sepsis, Kawasaki disease, or a Th2-associated disease, or any of the diseases described herein, is desirable in a variety of situations. For example, portable test kits could allow emergency medical personnel to evaluate a subject in the field, to determine whether they should be transported to the emergency department. Moreover, triage decisions, e.g., in an emergency department or other clinical setting, can also be made based on information provided by a method described herein. Those patients exhibiting increased human soluble ST2 levels can be prioritized over those with lower levels.

In some embodiments, the level of human soluble ST2 is determined once, e.g., at the time the subject is suspected of having a disease (e.g., upon presentation to a medical professional or health care facility). In some embodiments, the level of human soluble ST2 is determined at one or more of 2, 4, 6, 8, 12, 18, and/or 24 hours, and/or 1-7 days or more after the time the subject is suspected of having a disease (e.g., upon presentation to a medical profession or health care facility).

In some embodiments, the level of human soluble ST2 is determined more than once. In some embodiments where the level of human soluble ST2 is determined more than once, the highest level can be used, or the change in levels can be determined and used. Levels of human soluble ST2 can also be determined multiple times to evaluate a subject's response to a treatment. For example, a level of human soluble ST2 taken after administration of a treatment, e.g., one or more doses or rounds of a treatment, can be compared to levels of human soluble ST2 before the treatment was initiated, e.g., a baseline level. The change in human soluble ST2 levels would indicate whether the treatment was effective; e.g., a reduction in human soluble ST2 levels would indicate that the treatment was effective.

In some embodiments, the level of human soluble ST2 in a subject is assayed and compared to a human soluble ST2 reference level. Any of a variety of techniques known to those skilled in the art can be used to assay human soluble ST2 levels in a subject. Exemplary assay methods include, without limitation, methods known in the art such as quantitative PCR or Northern blot analysis. In some embodiments, the level of human soluble ST2 in a subject is assayed using immunoassays such as enzyme-linked immunosorbent assays (ELISA). For example, in some embodiments an antibody or antigen-binding fragment thereof described herein is contacted with a sample from the subject. A sample can comprise or be derived from any of a variety of cells or tissues of a subject. For example, a sample can include one or more of blood, serum, or plasma. Binding of the antibody or antibody fragment is then detected and optionally quantified, and levels of the protein are determined based on levels of antibody or antibody fragment binding. In some embodiments, a sample contains substantially no ST2L form of the ST2 protein, such that all or the majority of ST2 in the sample detected according to methods disclosed herein is human soluble ST2. In some embodiments, a sample contains no detectable ST2L, such that the only detectable ST2 in a sample is human soluble ST2. In some embodiments, a sample containing substantially no ST2L, or no detectable ST2L, is a serum or blood sample. In some embodiments, human soluble ST2 levels in a subject are assayed in immunoassays using at least one antibody or antigen-binding fragment described herein.

As described in more detail in the Examples section below, antibody compositions comprising antibodies produced by the hybridoma deposited at the ATCC and designated by Patent Deposit Designations PTA-10431 exhibits increased affinity for the human soluble ST2 antigen as compared to other commercially available antibodies. Such antibodies can be used in accordance with methods described herein.

The methods described herein are useful in determining that a subject does not have an ST2-associated condition. An ST2-associated condition is a condition that is associated with elevated levels of ST2. Certain exemplary ST2-associated conditions include, without limitation, cardiovascular disease, pulmonary disease, sepsis, Kawasaki disease, and Th2-associated diseases. ST2-associated conditions are generally serious and aggressive treatment is often indicated. Subjects exhibiting certain non-specific symptoms may or may not have an ST2-associated condition (e.g., cardiovascular disease, pulmonary disease, sepsis, Kawasaki disease, or a Th2-associated disease). Non-specific symptoms include, but are not limited to, chest pain or discomfort, shortness of breath, nausea, vomiting, eructation, sweating, palpitations, lightheadedness, fatigue, and fainting. Each symptom can have varied etiology.

In some embodiments, the methods described herein are useful in risk stratification, e.g., determining that a subject has a low-severity or low-risk form of an ST2-associated condition. For example, certain subjects having a cardiovascular disease (e.g., myocardial infarction or heart failure) are at low risk of adverse outcome, such as death or a recurring cardiac event, and also exhibit a lower concentration of human soluble ST2 than is observed in other subjects having a cardiovascular disease with a higher risk of adverse outcome. Such subjects can be considered to have a "low-severity" or "low-risk" form of an ST2-related cardiovascular condition. In both high-risk and low-risk populations, however, higher concentrations of human soluble ST2 are observed than are observed in subjects that do not have an ST-2 associated condition. Subjects having a low-severity form of an ST2-related condition typically have human soluble ST2 concentrations greater than a reference human soluble ST2 level (e.g., the median human soluble ST2 concentration of healthy or normal individuals), while subjects having a high-severity form of an ST2-related condition subjects typically have human soluble ST2 concentrations greater than the $80^{th}$ percentile of a reference human soluble ST2 level (e.g., human soluble ST2 concentrations observed in healthy or normal individuals). Determining that a subject exhibiting certain non-specific symptoms does not have, or has a low-severity form of, an ST2-associated condition can result in improved diagnosis and/or more effective treatment decisions, e.g., such a subject may not require aggressive treatment. For example, patients with elevated human soluble ST2 concentrations following acute myocardial infarction exhibited more cardiac remodeling (increased fibrosis) than patients with low human soluble ST2 concentrations, and eplerenone differentially attenuated cardiac remodeling in subjects that exhibited high human soluble ST2 concentrations (Weir et al., *J. Am. Coll. Cardiol.* 55:243-250, 2010). Thus, human soluble ST2 concentrations can be used to identify patients who should receive different, possibly non-standard, inpatient, or more aggressive treatment.

Chest Pain

Chest pain is the chief complaint in about 1 to 2 percent of outpatient visits, and although the cause is often non-cardiac, heart disease remains the leading cause of death in the United States. Therefore, distinguishing between serious and benign causes of chest pain is crucial. The methods described herein are useful in making this determination.

A subject presenting to the emergency department with chest pain may have esophageal pain, an ulcer, acute lung problems such as pulmonary embolus (PE) (potentially fatal), rupturing or dissecting aneurysm (highly lethal), gall bladder attack, pericarditis (inflammation of the sack around the heart), angina pectoris (cardiac pain without damage), or a myocardial infarction (potentially fatal). A precise diagnosis can be difficult to make immediately, but the decision whether to admit the subject or to treat the subject aggressively should generally be made immediately. If the methods described herein indicate that the subject has an elevated soluble ST2 level, e.g., suffers from an ST2-associated condition, the decision can be made to treat the subject aggressively, e.g., to prevent a potentially adverse outcome that would result from a lack of treatment. Additional information about treatment and diagnosis of chest pain can be found, e.g., in Cayley (*Am. Fam. Phys.* 72(10):2012-2028, 2005).

Dyspnea

Dyspnea, or shortness of breath (also defined as abnormal or uncomfortable breathing), is a common symptom of subjects on presentation to the emergency department. The differential diagnosis for dyspnea includes four general categories: (1) cardiac, (2) pulmonary, (3) mixed cardiac or pulmonary, and (4) non-cardiac or non-pulmonary.

Cardiac causes of dyspnea include right, left, or biventricular congestive heart failure with resultant systolic dysfunction, coronary artery disease, recent or remote myocardial infarction, cardiomyopathy, valvular dysfunction, left ventricular hypertrophy with resultant diastolic dysfunction, asymmetric septal hypertrophy, pericarditis, and arrhythmias.

Pulmonary causes include obstructive (e.g., chronic obstructive pulmonary disease (COPD) and asthma) and restrictive processes (e.g., extrapulmonary causes such as obesity, spine, or chest wall deformities, and intrinsic pulmonary pathology, such as interstitial fibrosis, pneumoconiosis, granulomatous disease, or collagen vascular disease). Mixed cardiac and pulmonary disorders include COPD with pulmonary hypertension and cor pulmonale, deconditioning, pulmonary emboli, ARDS, and trauma. Non-cardiac or non-pulmonary disorders include metabolic conditions such as anemia, diabetic ketoacidosis, and other, less common, causes of metabolic acidosis, pain in the chest wall or elsewhere in the body, and neuromuscular disorders such as multiple sclerosis and muscular dystrophy. Obstructive rhinolaryngeal problems include nasal obstruction due to polyps or septal deviation, enlarged tonsils, and supraglottic or subglottic airway stricture.

Dyspnea can also present as a somatic manifestation of psychiatric disorders, e.g., an anxiety disorder, with resultant hyperventilation. Additional information regarding the evaluation and treatment of dyspnea can be found, e.g., in Morgan and Hodge, *Am. Fam. Phys.* 57(4):711-718, 1998.

Any of the antibodies or antigen-binding fragments disclosed herein can be used in determining that a subject does not have an ST2-associated condition. In some embodiments, the level of human soluble ST2 in a subject is assayed (e.g., by any of the methods described above) and compared to a human soluble ST2 reference level. If the level of human soluble ST2 in a subject is similar to the human soluble ST2 reference level, it can be determined that the subject has a very low likelihood of having an ST2-associated condition. A level of human soluble ST2 in a subject is "similar to" a human soluble ST2 reference level when the two levels are sufficiently close in range such that the subject is not likely to have an ST2-associated condition. Generally, a level of human soluble ST2 in a subject is "similar to" a human soluble ST2 reference level when the two levels are within about 25% of each other, e.g., within about 25%, 20%, 15%, 10%, 5%, or lower. Those skilled in the art will be able to determine suitable human soluble ST2 reference levels for the ST2-associated condition at issue. Those skilled in the art will also be aware of normal variations in such human soluble ST2 levels, and upon reading the present disclosure, will be able to determine whether a determined human soluble ST2 level is similar to a human soluble ST2 reference level.

In some embodiments, the level of human soluble ST2 is determined once, e.g., at the time the subject is suspected of having an ST2-associated condition. In some embodiments, the level of human soluble ST2 is determined at one or more of 2, 4, 6, 8, 12, 18, and/or 24 hours, and/or 1-7 days after the time the subject is suspected of having an ST2-associated condition. In some embodiments, the level of human soluble ST2 is determined more than once, e.g., to confirm or check the level of human soluble ST2 determined in the first assay.

In some embodiments, the human soluble ST2-binding antibodies and antigen-binding fragments thereof described herein can be used in one or more methods described in U.S. Patent Application Publication Nos. US 2007/0248981, US 2009/0264779, US 2009/0305265, and US 2010/0009356, and PCT Application Publication No. WO2007/131031.

In some embodiments, methods of diagnosing a disease in a subject include obtaining a sample from a subject, determining a level of human soluble ST2 in the sample using at least one antibody or fragment described herein and a level of at least one (e.g., two, three, four, or five) additional marker, wherein an elevated level of human soluble ST2 in the sample compared to a reference level of human soluble ST2 and an altered (e.g., increased or decreased) level of the at least one additional marker relative to a reference level of the at least one (e.g., two, three, four, or five) additional marker, indicate that the subject has the disease (e.g., cardiovascular disease, a pulmonary disease, sepsis, Kawasaki disease, or a Th2-associated disease, or any other disease described herein). A reference level of the at least one additional marker can be the level of the marker in a subject not diagnosed as having the disease, the level of the marker in a subject not presenting with two or more symptoms of the disease, a subject not at risk of developing the disease, or level in the same subject at an earlier point in time. Additional markers are known in the art and methods for determining reference levels of additional markers can be determined by those skilled in the art.

In some embodiments, the reference levels of human soluble ST2 can be any of the reference levels described herein. Additional human soluble ST2 reference levels can be determined by those skilled in the art. In some embodiments, the sample contains blood, serum, or plasma. The sample can be obtained and the determination of the level of human soluble ST2 using at least one antibody or fragment described herein can be performed as described above.

Therapeutic Methods

In some embodiments, an ST2-binding antibody or antigen-binding fragment thereof is administered to a subject to treat any of a variety of diseases or conditions (e.g., any of the diseases described herein). For example, human soluble ST2 levels are elevated in subjects having diseases, such as, without limitation, cardiovascular disease, pulmonary disease, sepsis, Kawasaki disease, and/or Th2-associated diseases. Any of the human soluble ST2-binding antibodies or antigen-binding fragments thereof, as well as modified antibodies or antigen-binding fragments based on such antibodies or fragments (e.g., human, chimeric or humanized antibodies or fragments), can be used to treat such diseases or conditions.

In some embodiments, a subject is administered an antibody or antigen-binding fragment thereof that binds competitively with an antibody produced by a hybridoma deposited at the ATCC and designated by Patent Deposit Designation PTA-10431 or PTA-104312, or both. In some embodiments, a subject is administered an antibody or antigen-binding fragment described herein that is human, chimeric, or humanized. As is known in the art, such human, chimeric, or humanized antibodies and fragments are typically less immunogenic relative to non-human, non-chimeric, or non-humanized antibodies. Thus, such human, chimeric, or humanized antibodies and fragments offer therapeutic benefits such as, without limitation, decreased incidence of side effects, tolerance to increased doses, and improved pharmacokinetic and/or pharmacodynamic properties. In some embodiments, a human, chimeric, or humanized antibody or fragment to be administered to a subject is derived from an antibody produced a hybridoma deposited at the ATCC and designated by Patent Deposit Designation PTA-10431 or PTA-104312, or both. For example, the heavy and/or light chain variable regions of such antibodies can be joined to a human constant region or fragment thereof to create a chimeric antibody or fragment. Alternatively, or one or more CDRs (e.g., each of the CDRs) of such antibodies can be inserted into one or more human framework regions to create a humanized antibody or fragment.

In some embodiments, an anti-human soluble ST2 antibody or human soluble ST2-binding antibody fragment is administered to a subject directly. An anti-human soluble ST2 antibody or fragment can be administered in an amount effective, at dosages and for periods of time necessary to achieve the desired result. For example, a therapeutically active amount of antibody or fragment can vary according to factors such as the disease state, age, sex, and weight of the subject, and the ability of the antibody or fragment to elicit a desired response in the subject. Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of an anti-human soluble ST2 antibody or fragment to a subject. See e.g., *Physicians' Desk Reference,* 63rd edition, Thomson Reuters, Nov. 30, 2008.

Anti-human soluble ST2 antibodies or human soluble ST2-binding antibody fragments described herein can be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. Antibodies or fragments can include a delivery agent (e.g., a cationic polymer, peptide molecular transporter, surfactant, etc.) in combination with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations that contain an antibody or antigen-binding fragment thereof as described herein.

Kits

Also provided herein are kits that include a reagent comprising at least one (e.g., at least two, three, four, or five) anti-human soluble ST2 antibody or antigen-binding fragment described herein. Kits are generally comprised of the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can contain at least one (e.g., at least two, three, four, or five) of any of the antibodies or antigen-binding fragments described herein. For example, a kit can contain at least one (e.g., at least two, three, four, or five) antibody or antigen-binding fragment thereof that binds competitively with an antibody produced a hybridoma deposited at the ATCC and designated by Patent Deposit Designation PTA-10431 or PTA-104312, or both.

In some embodiments, a kit provided herein contains at least one (e.g., at least two, three, four, or five) anti-human soluble ST2 antibodies or antigen-binding fragments described herein, and one or more reagents for detecting binding of the antibody or antigen-binding fragment to human soluble ST2. For example, the kit can be designed for use in a chemiluminescent microparticle immunoassay (CMIA), such as the ARCHITECT assays from Abbot Diagnostics (Abbott Park, Ill.), and thus can contain paramagnetic microparticles coated with anti-BNP antibodies, and paramagnetic microparticles coated with anti-human soluble ST2 antibodies. These microparticles are contacted with a sample, and the human soluble ST2 present in the sample can bind to the coated microparticles. Optionally, the sample can be split into at least two aliquots, and each type of microparticle can be contacted with a separate aliquot. After washing, anti-human soluble ST2 acridinium-labeled conjugate can be added to create a reaction mixture in the second step. Following another wash cycle pre-trigger and trigger solutions are added to the reaction mixture. The resulting chemiluminescent reaction is measured, e.g., using the ARCHITECT i System optics (Abbot Diagnostics, Abbott Park, Ill.). A direct relationship exists between the amount of human soluble ST2 in the sample and the chemiluminescence detected.

In some embodiments, kit provided herein contain at least one (e.g., at least two, three, four, or five) anti-human soluble ST2 antibodies or antigen-binding fragments described herein, and one or more solid phase immunoassay components for detecting human soluble ST2 via solid phase analysis. Solid phase immunoassays employ a solid support to which one member of a ligand-receptor pair, e.g., an antibody or antigen-binding fragment thereof, is bound. Non-limiting examples of solid supports include plates, tubes, beads of polystyrene, and various porous materials such as, e.g., nylon, nitrocellulose, cellulose acetate, and glass fibers. See e.g., U.S. Pat. Nos. 4,703,017; 4,743,560; and 5,073,484. In some embodiments, a kit comprises components for a solid phase immunoassay, in which a solid phase-bound antibody or antigen-binding fragment thereof (e.g., an anti-human soluble ST2 antibody or antigen-binding fragment thereof) is contacted with a sample containing an analyte of interest (e.g., human soluble ST2), after which the solid phase is washed to remove unbound material.

In some embodiments, a kit contains components for a flow-through solid phase immunoassay. Flow-through solid phase immunoassays obviate the need for incubation and washing steps associated with other types of solid phase immunoassays. A variety of flow-through solid phase immunoassays are known in the art. For example, U.S. Pat. No. 4,632,901, discloses a flow-through immunoassay device wherein an antibody (specific to a target antigen analyte) is bound to a porous membrane or filter to which a liquid sample is added. As the liquid flows through the membrane, target analyte binds to the antibody. The addition of sample is followed by addition of labeled antibody. The visual detection of labeled antibody provides an indication of the presence of target antigen analyte in the sample. Moreover, U.S. Pat. No. 5,229,073, describes a semiquantitative competitive immunoassay lateral flow method that employs a plurality of capture zones or lines containing immobilized antibodies for measuring plasma lipoprotein levels. Additional examples of lateral-flow tests for detecting analytes are disclosed in U.S. Pat. Nos. 4,168,146; 4,366,241; 4,703,017; 4,855,240; 4,861,711; and 5,120,643; European Patent No. 0296724; WO 97/06439; and WO 98/36278. Those skilled in the art will be aware of other suitable solid phase immunoassay methods and devices, and will be able to employ one or more of the anti-human soluble ST2 antibodies and antigen-binding fragments described herein in such methods and devices.

In some embodiments, other methods of detection can be used, e.g., colorimetric assays, radioimmunoassays, or chemiluminescent assays. Sandwich assays can be used as well, e.g., using two monoclonal antibodies, one labeled with iodine 125 and the other adsorbed onto beads, e.g., as used in the IRMA-BNP2 kit from CISBIO International (France) and the ShionoRIA BNP or ANP kits (SHIONOGI USA Inc.).

Kits as provided herein can be used in accordance with any of the methods (e.g., diagnostic methods) described above. For example, kits containing at least one (e.g., at least two, three, four, or five) anti-human soluble ST2 antibody or antigen-binding fragment thereof described herein can be used to determine the level of human soluble ST2 in a sample. Moreover, kits containing at least one (e.g., at least two, three, four, or five) anti-human soluble ST2 antibody or antigen-binding fragment thereof can be used to determine a human soluble ST2 reference level. Those skilled in the art will be aware of other suitable uses for kits provided herein, and will be able to employ the kits for such uses.

In some embodiments of the kits, at least one (e.g., one, two, three, or four) of the antibodies or fragments has a $K_D$ for binding to human soluble ST2 equal to or less than $8.59 \times 10^{-10}$ M. In some embodiments of the kits, the kit is provided as an enzyme-linked immunosorbent assay. Some embodiments of the kits further contain a recombinant human soluble ST2 isolated from a human cell (e.g., a human embryonic kidney cell). Some embodiments of the kits further contain a fully glycosylated human soluble ST2 (e.g., present in a cell extract or provided as an isolated protein).

EXAMPLES

The invention is further described in the following examples, which do not limit the scope of the invention described in the claims.

Example 1

Production and Characterization of Anti-ST2 Monoclonal Antibodies

Monoclonal antibodies to the human soluble ST2 (sST2) protein were produced by immunizing mice with recombinant protein produced from the human cDNA sequence for sST2.

Antigen Production and Confirmation: A human sST2 cDNA clone, GeneBank Accession Number NM_003856.2, was purchased from Origene Technologies, Inc. of Rockville, Md. Using standard PCR techniques, this clone was used as the source sequence to create an expression vector including the entire human soluble ST2 sequence with a hexa-histidine purification tag incorporated in the amino-terminus region of the protein. Integrity of the expression clone was confirmed by DNA sequencing. Recombinant protein was produced by transient transfection and expression in human embryonic kidney cells (HEK293). Recombinant human soluble ST2 protein was purified by passing cell lysate over a metal chelate column specifically binding the histidine purification tag incorporated into the expressed protein. Purification of recombinant human soluble ST2 was confirmed by Coomassie stained polyacrylamide gel and by Western blot analysis using both commercially available anti-ST2 antibodies (monoclonal antibody D067 obtained from MBL International) as well as anti-His tag antibodies. See, FIGS. 1, 2, and 3A-3C. The protein itself has a molecular weight of 36 kD, based on the amino acid sequence, and it was shown by Kuroiwa et al. (*Biochem. Biophys. Res. Comm.* 284:1104-1108, 2001), that the native protein in human serum has a molecular weight of ~58 kD. The purified recombinant protein produced from this expression system had the appropriate molecular weight of ~58 kD for a fully glycosylated protein and was appropriately recognized by commercially available anti-ST2 antibodies. Quantification was performed by Bradford total protein assay.

Hybridoma and Monoclonal Antibody Production: Monoclonal antibodies were produced by immunizing mice with recombinant protein produced as described above. Three Balb/c mice were immunized as follows:

| T1 | 20 µg/animal with CFA (complete Freund's Adjuvant) |
| T1 + 3 days | 20 µg/animal with IFA (incomplete Freund's Adjuvant) |
| T1 + 6 days | 20 µg/animal in Saline |
| T1 + 9 days | 20 µg/animal in Saline |

Figure 4:
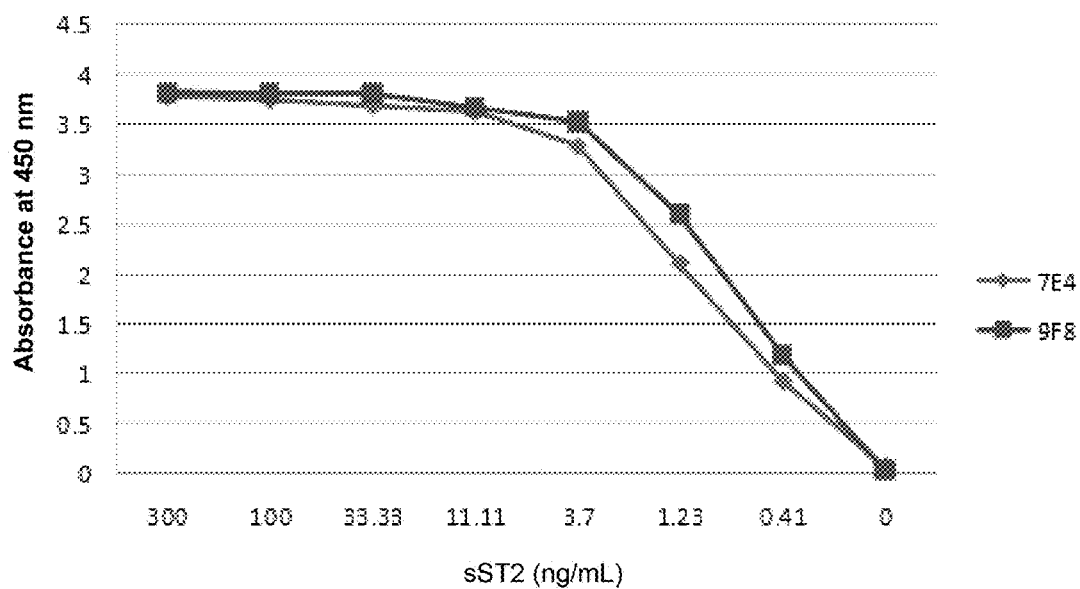
FIG. 4 is a line graph showing the results of an antigen sensitivity assessment of the 7E4 and 9F8 antibodies.

After the final immunization antibody titer was determined from a tail bleed from each animal. The animal with the highest antibody titer was used for splenic fusion and hybridoma establishment. After establishing the hybridomas as stable cell cultures in 96-well plates, they were screened for binding to the recombinant human soluble ST2 protein and to a generic protein containing a hexa-his purification tag to eliminate hybridomas specific to this tag. Two hybridomas were selected for additional characterization and product development: 7E4 and 9F8. Both monoclonal antibodies were tested for sensitivity to the recombinant human soluble ST2 antigen by coating individual wells of 96-well microtiter plates with consistent quantities of each antibody, 9F8 and 7E4, then tested against 3-fold serial dilutions of biotin-conjugated recombinant human soluble ST2, concentration range of 300 to 0.41 ng/mL (see FIG. 4.)

Figure 5:
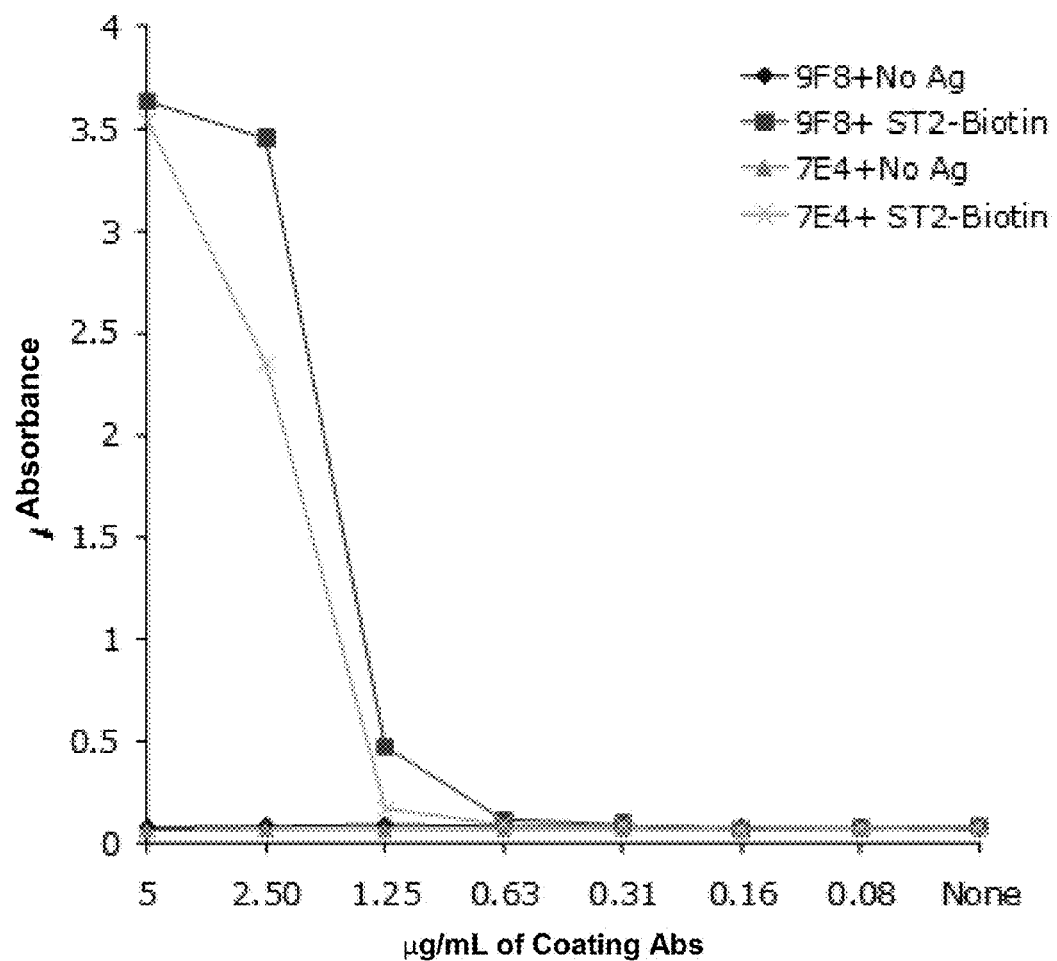
FIG. 5 is a line graph showing the results of an antigen sensitivity assessment of the 7E4 and 9F8 antibodies. The 7E4 and 9F8 antibodies were coated into individual wells of a 96-well plate at concentrations ranging from 5 μg/mL to 0 and tested against a single concentration of biotin-conjugated recombinant soluble ST2.

The two antibodies illustrate comparable analyte sensitivity with a very strong absorbance value, ~1.0, observed at the lowest analyte concentration tested, 0.41 ng/mL. Additionally, both antibodies were coated into individual wells of a 96-well plate at concentrations ranging from 5 µg/ml to 0 and tested against a single concentration of biotin-conjugated recombinant human soluble ST2 (see FIG. 5). Both antibodies exhibit significant sensitivity at a concentration of ≧1.25 µg/ml with antibody 9F8 illustrating slightly greater sensitivity.

Figure 6:
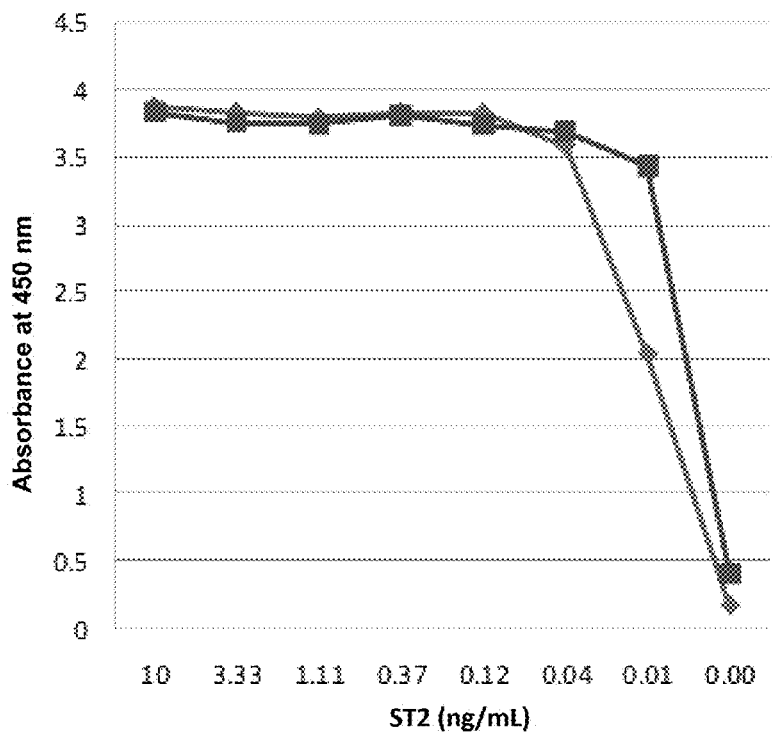
FIG. 6 is a line graph showing the results of testing for their ability to be used together in a monoclonal antibody sandwich enzyme immunoassay (EIA) configuration, wherein either the 7E4 or the 9F8 antibody was biotinylated.
Figure 7A:
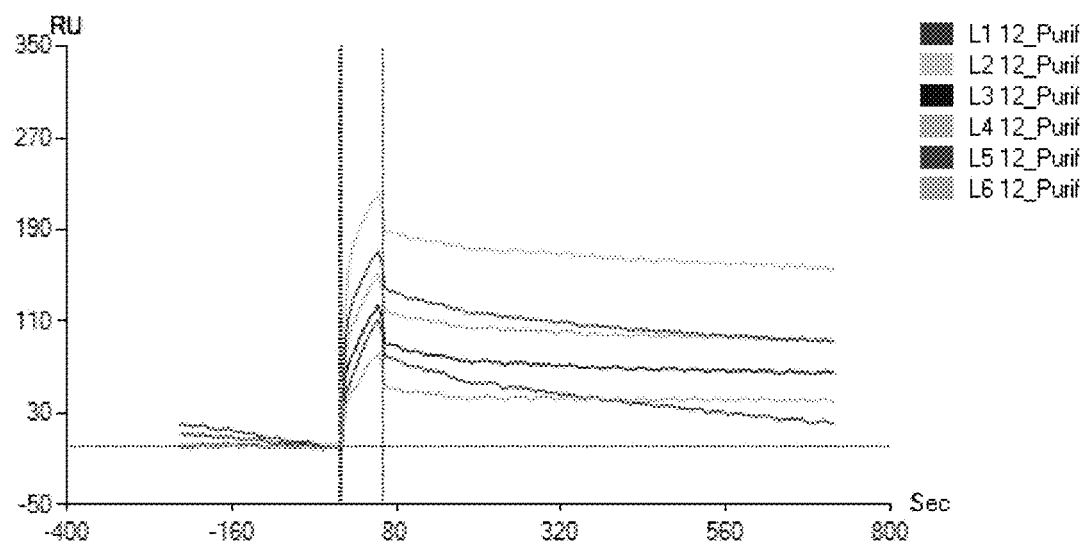
FIGS. 7A-7F are six graphs showing the results of surface plasmon resonance (SPR) analysis of antibody-antigen complex formation.
Figure 7B:
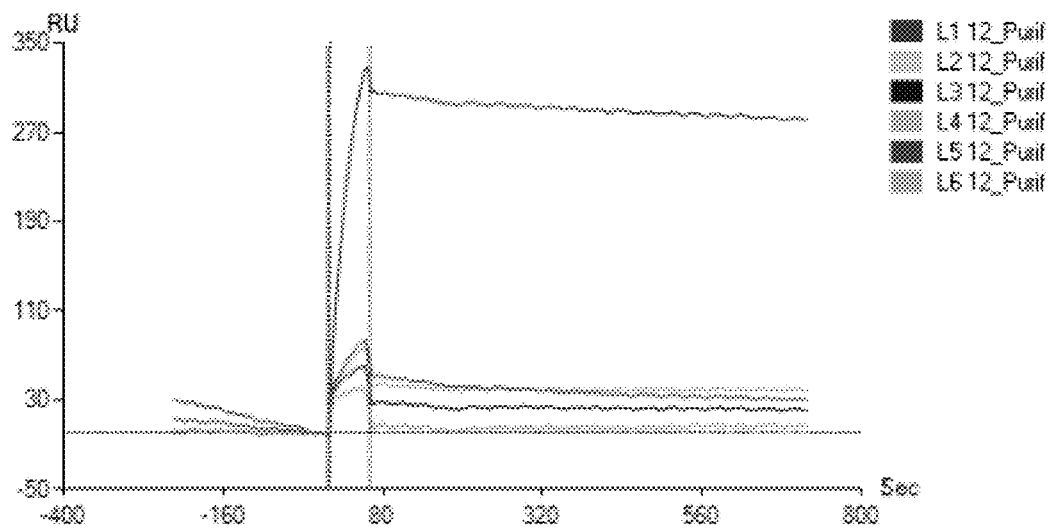
Figure 7C:
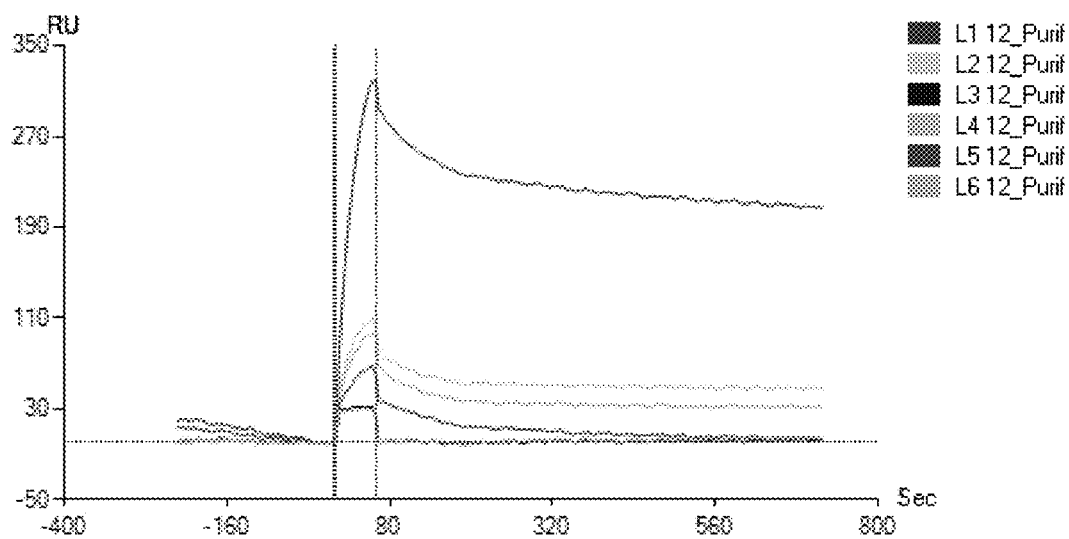
Figure 7D:
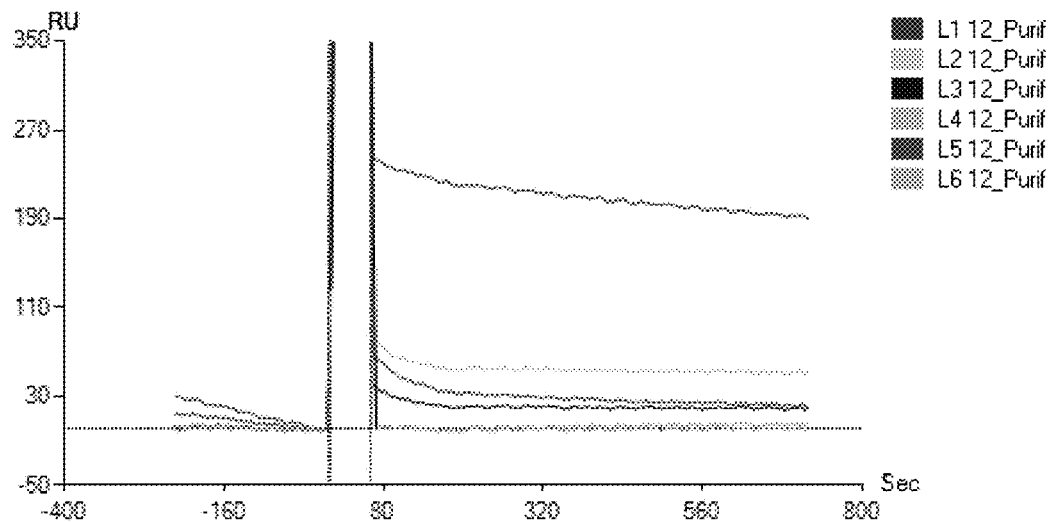
Figure 7E:
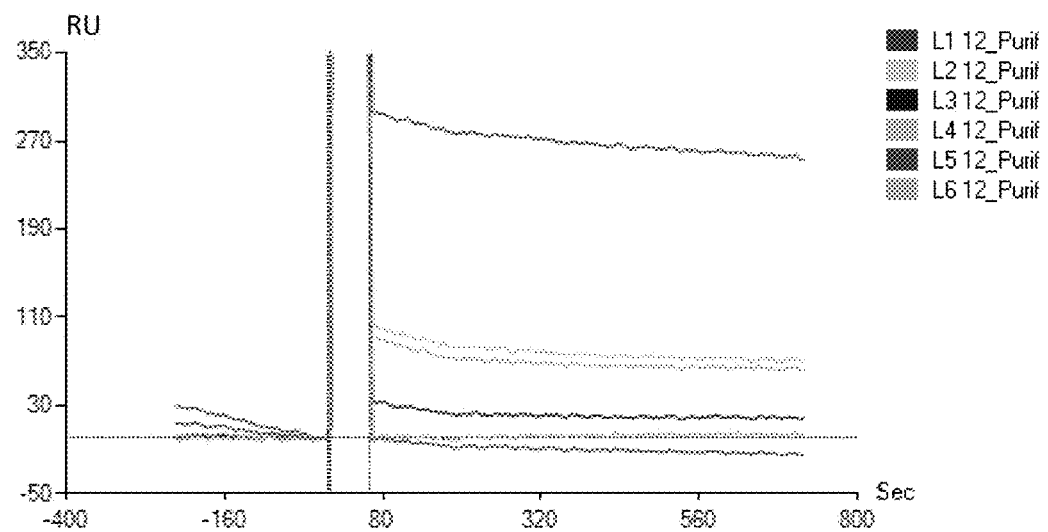
Figure 7F:
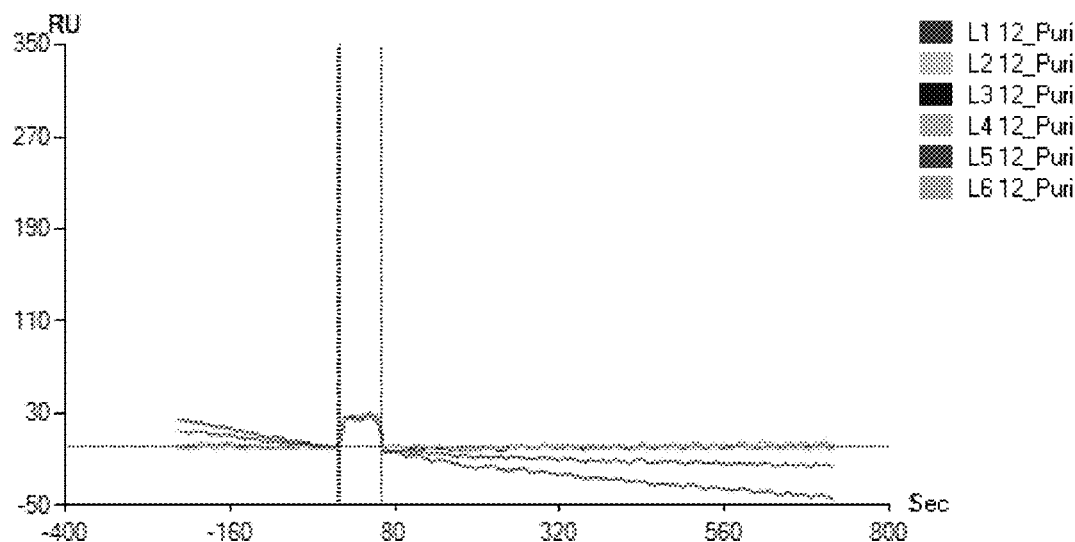
Figure 8A:
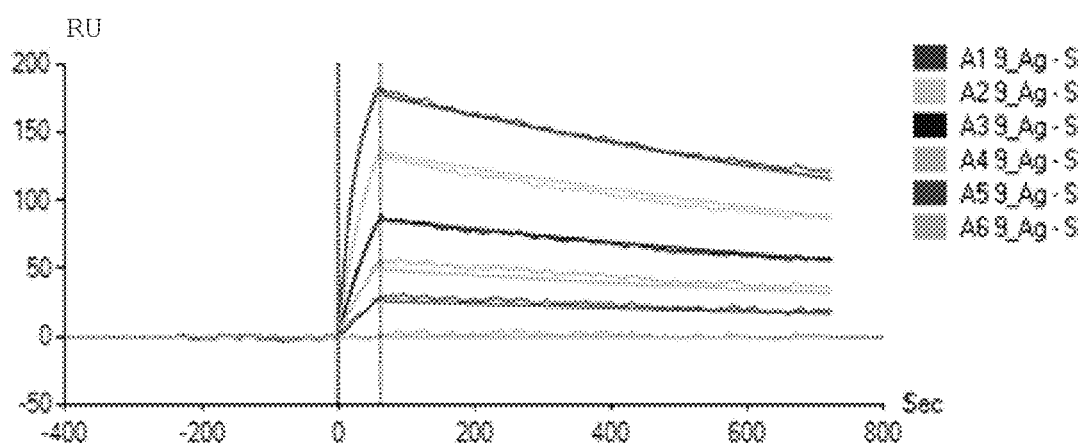
FIGS. 8A-8F are six graphs showing the results of SPR analysis of antibody-antigen complex formation.
Figure 8B:
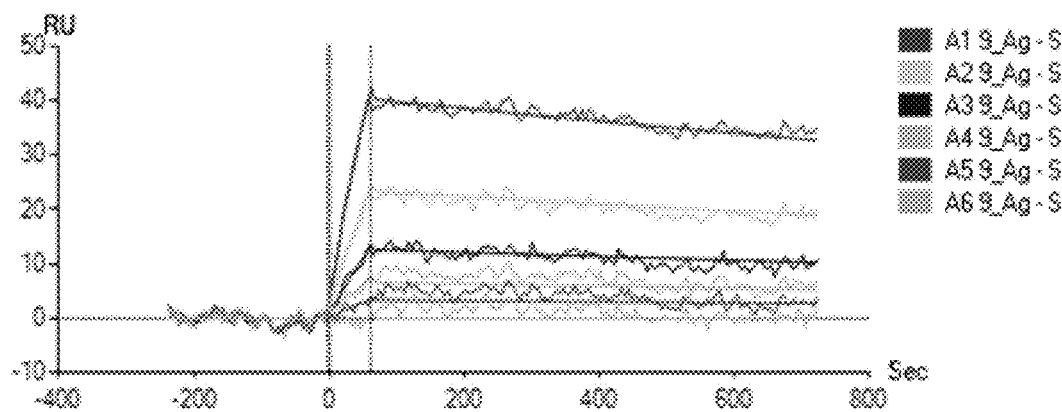
Figure 8C:
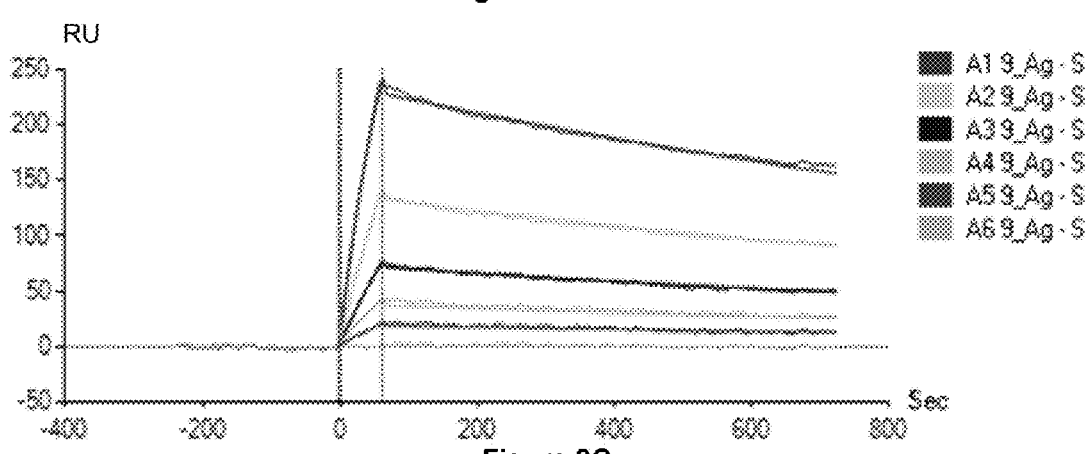
Figure 8D:
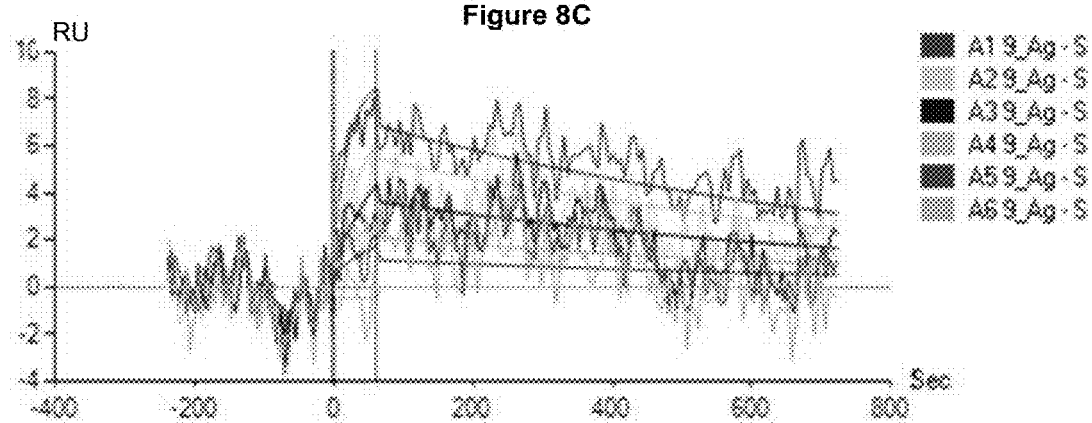
Figure 8E:
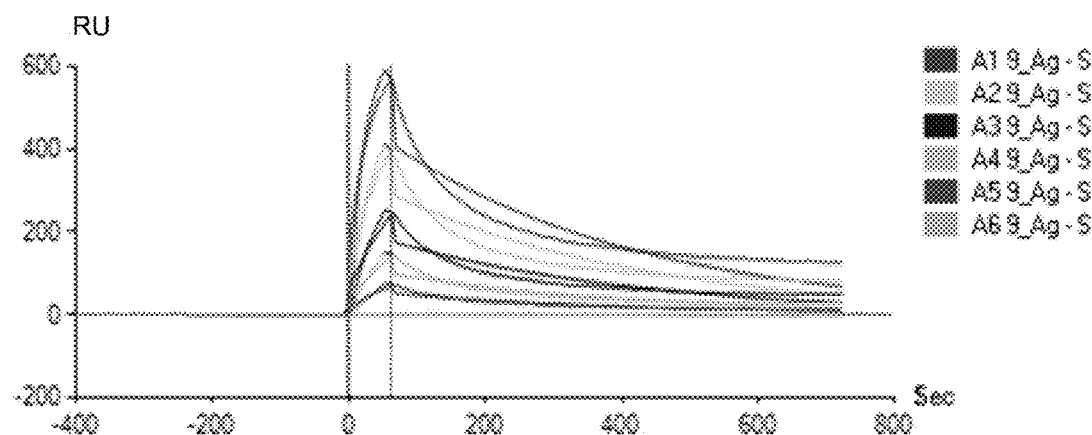
Figure 8F:
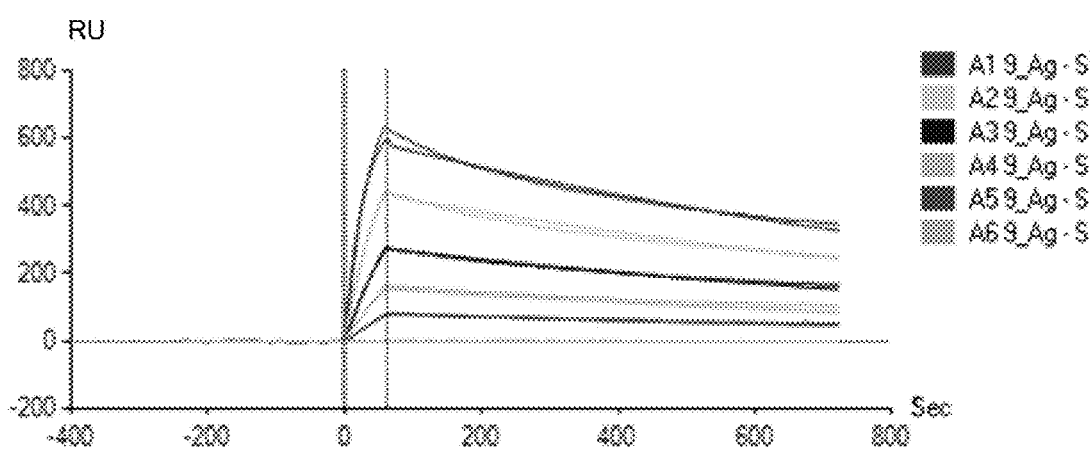
Figure 9:
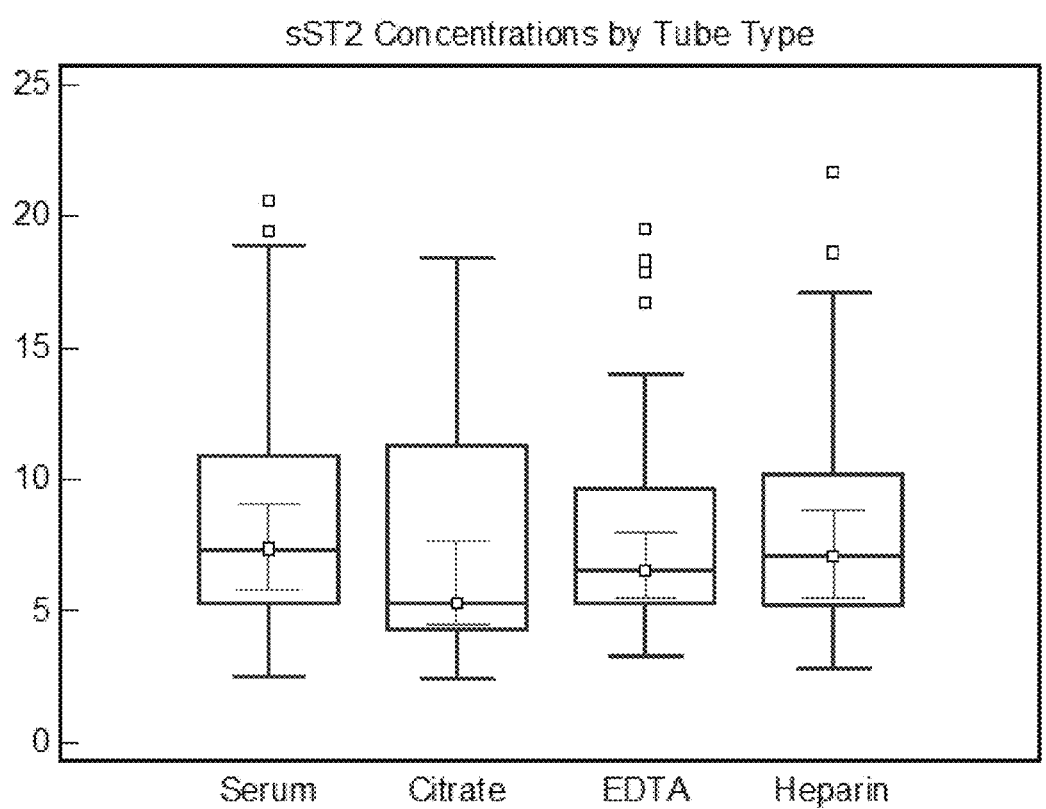
FIG. 9 is a box-whisker plot showing human soluble ST2 concentrations by anticoagulant tube type.

The 9F8 and 7E4 antibodies were also tested for their ability to be used together in a monoclonal antibody sandwich enzyme immunoassay (EIA) configuration. Each monoclonal antibody was coated in individual wells of a 96-well microtiter plate at a constant concentration and assayed against a 3-fold serial dilution range of human soluble sST2 concentrations, from 10 ng/ml to 0.01 ng/ml, using the other monoclonal antibody conjugated with biotin for detection of the complex. As shown in FIG. 6, both antibody combinations result in comparable sensitivity and readily detect as little as 0.01 ng/mL human soluble ST2.

Additional analysis using surface plasmon resonance (SPR) confirmed that antibodies 9F8 and 7E4 each recognize unique epitopes and epitopes that are different than are recognized by the commercially available antibodies D066 and D067, the monoclonal antibodies used by MBL International Corporation (MBL) in their ELISA. FIG. 7 illustrates the results of a SPR analysis of antibodies 9F8, 7E4, a third novel anti-human soluble ST2 antibody included for reference (11A7), both monoclonal antibodies commercially available from MBL (D066 and D067), plus an irrelevant antibody for baseline determination. An individual SPR chip was prepared with a coating for each monoclonal antibody. Recombinant human soluble ST2 was flowed across the chip and allowed to bind. Then the test monoclonal antibodies were flowed across the first antibody-human soluble ST2 complex to assess whether the second antibody could also bind to the complex through the human soluble ST2 protein. Only secondary antibodies that recognize a different epitope than the primary antibody will bind to the complex.

The results of the SPR analysis are shown in FIGS. 7A-F.

Graph A1 (FIG. 7A): When antibody 9F8 (A1) was used as the primary capture antibody, each test antibody demonstrated at least a minimal measurable signal. Test antibody 7E4 (L2) had the highest signal, the irrelevant antibody (L6) had the lowest signal. The conclusion from this graph is that antibody 9F8 recognized a different epitope than any of the test antibodies and that the 9F8-7E4 pair provided the strongest overall binding.

Graph A2 (FIG. 7B): When antibody 7E4 (A2) was used as the primary capture antibody test antibody, 9F8 (L1) showed very good binding, the irrelevant antibody showed no measurable signal and the remaining test antibodies showed a low, but measurable, signal. The conclusion from this graph is that antibody 7E4 recognizes a different epitope than any of the test antibodies and that the 9F8-7E4 pair provided the strongest overall binding.

Graph A3 (FIG. 7C): When novel antibody 11A7 (A3) was used as the primary capture antibody test antibody, 9F8 (L1) showed very good binding, the irrelevant antibody showed no measurable signal and the remaining test antibodies showed a low, but measurable, signal. These results were almost identical to the results generated using antibody 7E4 as the capture antibody.

Graph A4 (FIG. 7D): When MBL antibody D066 (A4) was used as the primary capture antibody test antibody, 9F8 (L1) showed very good binding, followed in binding strength by antibody 7E4 (L2). The irrelevant antibody showed no measurable signal and the remaining test antibodies showed a low but measurable signal. The conclusion from this graph is that antibody D066 recognized a different epitope than any of the test antibodies, and that it formed a binding pair with the second MBL antibody, D067, but with much lower binding affinity than the 9F8-7E4 pair.

Graph A5 (FIG. 7E): When MBL antibody D067 (A5) was used as the primary capture antibody test antibody, 9F8 (L1) showed very good binding, followed in binding strength by antibodies 7E4 (L2) and D066 (L4). The irrelevant antibody showed no measurable signal and antibody 11A7 showed very low signal. The conclusion from this graph is that antibody D067 recognized a different epitope than any of the test antibodies, and that it formed a binding pair with the second MBL antibody, D066, but with much lower binding affinity than the 9F8-7E4 pair.

Graph A6 (FIG. 7F): When the irrelevant antibody was used as the primary test antibody there was no measurable signal generated from any of the test antibodies, confirming the specificity of the antibodies tested for affinity to human soluble ST2.

This analysis confirmed that the novel anti-human soluble ST2 monoclonal antibodies 9F8 and 7E4 recognized different epitopes than either of the MBL monoclonal antibodies D066 and D067. Further, this analysis also confirmed that the 9F8-7E4 pair had a higher binding affinity that the D066-D067 pair.

This increased binding affinity observed for the 9F8-7E4 pair was confirmed in head to head comparison of the two monoclonal antibody pairs in testing human plasma samples. In the experiment summarized in Table 1, the MBL ELISA comprised of the antibody pair D066-D067 was compared to the novel 9F8-7E4 antibody pair. Four (4) plasma samples were tested in a 2-fold dilution series, a matched pair of EDTA plasma and heparin plasma from a low human soluble ST2 concentration donor, and both EDTA plasma and heparin plasma samples from an elevated human soluble ST2 concentration donor were used.

Example 2

EIA Characterization for 9F8-7E4 Monoclonal Antibody Pair

The characteristics of the 9F8-7E4 monoclonal antibody pair were analyzed in an enzyme immunoassay (EIA).

Functional Sensitivity (limit of quantitation): The functional sensitivity limit was determined by assaying various concentrations of diluted calibrator in replicates of 20. In addition to the buffer blank, concentrations of calibrator tested included 0.0625, 0.125, and 0.25 ng/mL. Functional sensitivity is defined as the lowest concentration resulting in a CV≦20%. As shown in the following Table 2, all concentrations tested met this criteria with the lowest concentration tested being 0.0625 ng/mL.

TABLE 2

Functional Sensitivity Analysis Summary

| ST2(ng/mL) | Mean $A_{450}$ | Std Dev | CV % |
|---|---|---|---|
| 0.0 | 0.137 | 0.020 | 14.% |
| 0.065 | 0.222 | 0.038 | 17.% |
| 0.125 | 0.297 | 0.011 | 3.7% |
| 0.25 | 0.471 | 0.026 | 5.5% |

SPR was also used to determine the affinity of four antibodies produced by the methods described herein (9F8, 7E4,

TABLE 1

Comparison of Sensitivity of D066-D067 and 9F8-7E4 with Human Plasma Samples

| dilution factor | LS EDTA | | LS heparin | | HS EDTA | | HS heparin | |
|---|---|---|---|---|---|---|---|---|
| | D066-D067 | 9F8-7E4 | D066-D067 | 9F8-7E4 | D066-D067 | 9F8-7E4 | D066-D067 | 9F8-7E4 |
| 2 | 0.27 | EUL | ND | EUL | 0.86 | EUL | 0.29 | EUL |
| 4 | 0.45 | 19.7 | ND | 22.7 | 1.20 | EUL | 0.53 | EUL |
| 8 | ND | 20.4 | ND | 22.3 | 1.65 | EUL | 1.14 | EUL |
| 16 | ND | 21.6 | ND | 23.6 | 2.40 | EUL | 1.95 | EUL |
| 32 | ND | 23.5 | ND | 26.6 | 3.89 | 158.1 | ND | 134.0 |
| 64 | ND | 23.5 | ND | 26.6 | ND | 154.9 | ND | 136.3 |
| 128 | ND | 24.3 | ND | 27.3 | ND | 172.1 | ND | 152.4 |
| 256 | ND | 23.9 | ND | 30.4 | ND | 189.3 | ND | 160.8 |
| mean | 0.36 | 22.4 | | 25.6 | 2.00 | 168.6 | 0.98 | 145.9 |
| CV | 37% | 8.1% | | 11.4% | 60% | 9.3% | 76% | 8.8% |

LS = low sST2 concentration sample, HS = high sST2 concentration sample, ND = not detected, EUL = exceeds upper limit of detection The results in Table 1 were generated by using each assay optimized for its individual performance with results reported in ng/mL based on the calibrator optimized for each antibody pair. The mass amounts reported here do not match as the calibrator proteins were not normalized to each other but were quantified independently. As shown in Table 1 the detection limit for the D066-D067 pair was the 1:4 dilution of the LS EDTA sample, and with poor precision, while the 9F8-7E4 pair was able to accurately measure down to a 1:256 dilution with good precision, CV<10%. This sensitivity difference is consistent when the HS EDTA plasma sample was tested. Also of note, the D066-D067 pair was not able to detect even the least dilute LS heparin plasma sample, and with the HS samples the heparin plasma sample had much lower signal than the EDTA plasma sample with the D066-D067 pair, indicating a sensitivity or inhibition of this antibody pair by heparin. The 9F8-7E4 pair did not exhibit this heparin sensitivity and maintained good precision, low CV, in both the low and high human soluble ST2 concentration test plasma samples.

11A7, and 15D06), and two antibodies produced by MBL International (D066-3 and D067-3). Each experiment was performed by detecting the binding of the following concentrations of the recombinant human soluble ST2 protein used to prepare the 9F8 and 7E4 antibodies described herein: 50 nM, 25 nM, 12.5 nM, 6.25 nM, 3.25 nM, and 0 nM. The data of these experiments are shown in FIGS. 8A-8F. The calculated $K_D$ of each antibody for binding to recombinant human soluble ST2 isolated from human embryonic kidney cells is shown in Table 3.

TABLE 3

The $K_D$ of binding of each antibody for human soluble ST2.

| mAb | $K_D$ (M) |
|---|---|
| 9F8 | 8.59E−10 |
| 7E4 | 1.51E−09 |
| 11A7 | 2.72E−09 |

TABLE 3-continued

The $K_D$ of binding of each antibody for human soluble ST2.

| mAb | $K_D$ (M) |
|---|---|
| 15D6 | 1.32E−09 |
| D066 | 4.58E−09 |
| D067 | 1.24E−09 |

Precision: Precision evaluation of the assay was performed according to the Clinical and Laboratory Standards Institute (CLSI) guideline Evaluation of Precision Performance of Quantitative Measurement Methods: Approved Guideline-Second Edition. (InVitro Diagnostics) EP5-A2. Three pooled patient plasma samples were aliquoted into twenty 1.5-mL plastic tubes for each concentration level and frozen at −80° C. These samples were analyzed in duplicate in one run per day for 20 days within 2 months of blood collection. Within-run and total analytical imprecision ($CV_A$) was calculated with the CLSI single-run precision evaluation test. The assay had a within-run $CV_A$ of 2.4% and a total $CV_A$ of 4.0% at a mean concentration of 11 ng/mL (pool 1, low), a within-run $CV_A$ of 2.0% and a total $CV_A$ of 3.9% at a mean concentration of 87 ng/mL (pool 2, medium), and a within-run $CV_A$ of 2.2% and a total $CV_A$ of 3.9% at a mean concentration of 140 ng/mL (pool 3, high). See Table 4.

TABLE 4

Precision Analysis Summary

| Pool | Mean (ng/ml) | Within run CV | Total CV |
|---|---|---|---|
| low | 10.56 | 2.42% | 3.96% |
| Medium | 87.00 | 2.31% | 3.87% |
| high | 140.05 | 2.24% | 3.86% |

The assay does not exhibit any precision bias through the tested concentration range.

Interfering Substances (Sensitivity to Anticoagulant) Evaluation: In thirty apparently healthy volunteers, plasma samples were drawn in the most common tube types: serum, EDTA plasma, citrate plasma, and heparin plasma. Analysis was performed immediately following normal centrifugation and processing of the samples in a single human soluble ST2 analysis kit. The volunteers consisted of 9 males and 21 females with ages of 22-66 years. The results from this analysis are summarized in Table 5. As noted in Table 5, the median value for the citrate tube was slightly lower than for the other tube types, which is not unexpected as citrate tubes have a small volume of liquid anticoagulant in the tube that introduces a modest dilution of the collected sample relative to the other tube types that do not influence the sample volume. To test the consistency of measurements, each plasma tube type was compared to the serum tube. Each comparison resulted in a highly significant $R^2$ value, ranging from 0.849 to 0.964. Thus, with the exception of modest dilution in citrate tubes which may influence normal concentration measurements, there was no measured bias by tube type.

TABLE 5

Summary of Anticoagulant Test Results

| | | | sST2 (ng/ml) | | | |
|---|---|---|---|---|---|---|
| Patient ID | Age | Gender | Serum | Citrate Plasma | EDTA Plasma | Heparin Plasma |
| 1 | 24 | F | 7.4 | 13.7 | 6.3 | 3.9 |
| 2 | 26 | F | 5.7 | 7.3 | 7.2 | 8.8 |
| 3 | 62 | M | 7.9 | 6.6 | 8.0 | 4.3 |
| 4 | 45 | F | 6.8 | 5.2 | 6.3 | 6.7 |
| 5 | 41 | F | 5.3 | 4.3 | 5.5 | 5.3 |
| 6 | 53 | M | 6.3 | 5.3 | 7.3 | 7.9 |
| 7 | 56 | F | 2.5 | 2.4 | 3.3 | 3.2 |
| 8 | 50 | F | 6.4 | 4.8 | 5.8 | 6.5 |
| 9 | 44 | F | 7.7 | 5.1 | 5.6 | N/A |
| 10 | 63 | F | 4.9 | 3.7 | 5.1 | 4.9 |
| 11 | 66 | M | 7.4 | 5.1 | 6.8 | 7.4 |
| 12 | 57 | F | 9.1 | 6.9 | 7.9 | 8.8 |
| 13 | 59 | F | 5.0 | 4.3 | 4.2 | 4.2 |
| 14 | 52 | F | 6.0 | 4.5 | 5.8 | 6.4 |
| 15 | 58 | M | 20.6 | 17.7 | 19.5 | 17.1 |
| 16 | 22 | F | 6.0 | 2.8 | 5.3 | 6.6 |
| 17 | 49 | F | 13.7 | 12.4 | 12.7 | 11.9 |
| 18 | 29 | F | 5.2 | 4.8 | 5.2 | 7.9 |
| 19 | 35 | F | 3.9 | 3.2 | 3.5 | 3.4 |
| 20 | 24 | F | 8.2 | 6.5 | 7.3 | 7.1 |
| 21 | 50 | F | 13.1 | 11.2 | 11.6 | 11.7 |
| 22 | 54 | F | 10.9 | 7.5 | 9.7 | 9.7 |
| 23 | 49 | M | 18.9 | 14.0 | 17.9 | 18.6 |
| 24 | 53 | M | 15.4 | 12.5 | 16.7 | 13.0 |
| 25 | 64 | M | 7.3 | N/A | 5.1 | 6.0 |
| 26 | 51 | M | 15.1 | 11.4 | 14.0 | 14.5 |
| 27 | 27 | M | 19.4 | 18.4 | 18.3 | 21.7 |
| 28 | 22 | F | 9.0 | 7.6 | 7.4 | 8.2 |
| 29 | 56 | F | 2.7 | 2.5 | 3.3 | 2.8 |
| 30 | 52 | F | 4.8 | 3.8 | 5.5 | 5.5 |
| sST2 (ng/ml) by tube type: median | | | 7.3 | 5.3 | 6.5 | 7.1 |
| correlation with serum value: Rsq | | | | 0.849 | 0.964 | 0.891 |

Normal Concentration Reference Interval Determination: A cohort comprised of 490 donors, self-described as healthy with no known serious illness nor currently being treated for any serious illness, equally distributed between the genders and with age representation from 18 to 84 years, were recruited for this analysis.

Figure 10:
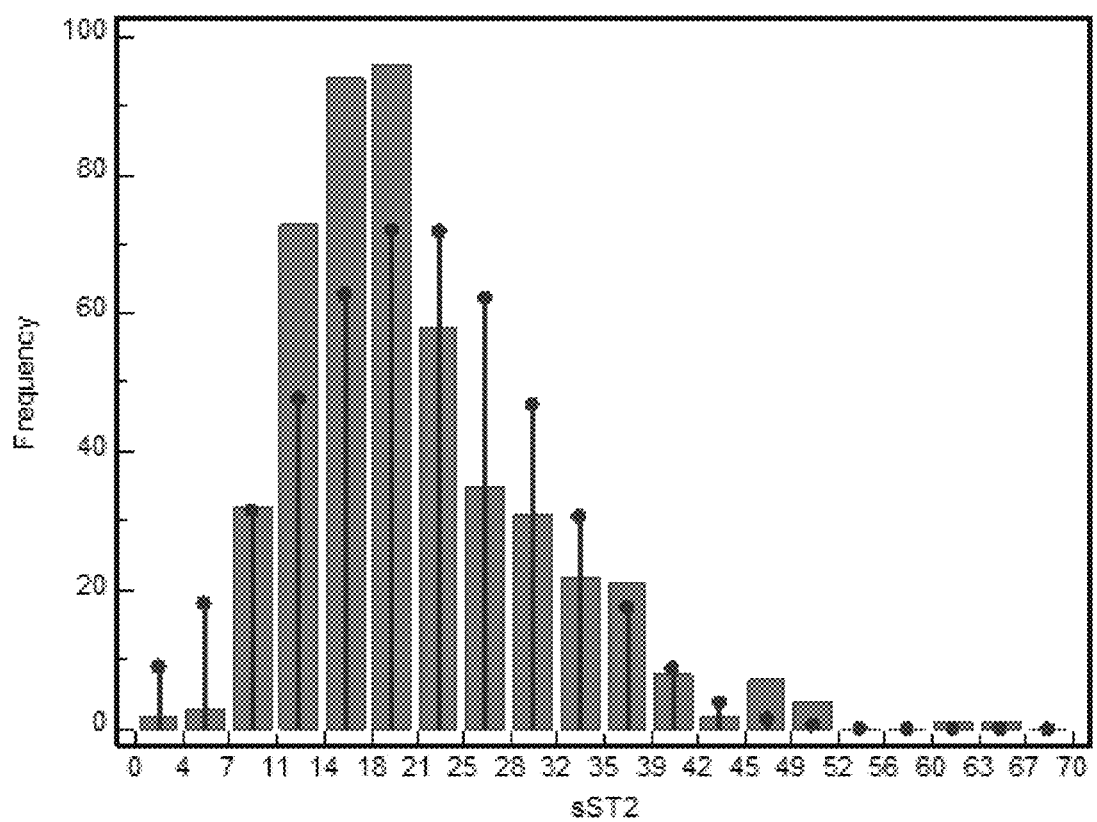
FIG. 10 is a histogram showing human soluble ST2 concentration distribution of normal healthy donors.

Table 6 provides a summary of the number of individuals in each age group and by gender for this healthy reference range cohort, and FIG. 10 is a histogram of the human soluble ST2 concentration distribution. In FIG. 10, the bars represent the actual data and the vertical lines inside the bars represent a theoretical normal distribution. The distribution of concentrations in these healthy individuals was non-normal. Table 7 compares human soluble ST2 concentrations as a function of gender. In this normal, healthy population, the median concentration in males was significantly greater than in females (Kruskal-Wallis test; $p<0.0001$).

TABLE 6

Healthy Reference Range Cohort

| | Number of individuals per age decade | | | | | | |
|---|---|---|---|---|---|---|---|
| | <30 | 30-39 | 40-49 | 50-59 | 60-69 | >70 | total |
| Female | 61 | 35 | 53 | 39 | 38 | 19 | 245 |
| Male | 65 | 47 | 40 | 41 | 31 | 21 | 245 |
| Total | 126 | 82 | 93 | 80 | 69 | 40 | 490 |

TABLE 7

Comparison of reference groups by median values by gender

| | Median (ng/mL) | 95% CI | IQR |
|---|---|---|---|
| Male | 23.6 | 21.3-25.1 | 17.6-30.6 |
| Female | 16.2 | 15.3-17.4 | 12.4-19.9 |

Figure 11:
FIG. 11 is a box-whisker plot showing human soluble ST2 concentrations as a function of gender and age in normal healthy donors.

Stratifying human soluble ST2 concentrations by age revealed that there were no significant differences across these groups, FIG. 11 (Kruskal-Wallis test; males p=0.501, females p=0.056). Thus, gender-specific reference values as well as entire group values were calculated using a non-parametric percentile method (90% single-sided). These results are summarized in Table 8.

TABLE 8

CCD Healthy Reference Group Summary

| Parameter/Group | Entire Group | Male | Female |
|---|---|---|---|
| N | 490 | 245 | 245 |
| Mean sST2 (ng/mL) | 20.9 | 24.9 | 16.9 |
| Median sST2 (ng/mL) | 18.8 | 23.6 | 16.2 |
| 95% confidence interval of median | 18.1-19.9 | 21.3-25.1 | 15.3-17.4 |
| Interquartile range | 14.5-25.3 | 17.6-30.6 | 12.4-19.9 |
| Upper Limit: 90% (95% CI) | 34.4 (32.4-35.8) | 37.4 (35.5-41.1) | 23.7 (22.2-25.9) |

Table 9 lists the human soluble ST2 concentration at several specific thresholds.

TABLE 9 sST2 Concentrations at Specific Thresholds US Self-Reported Healthy Cohort

| | Entire Cohort | | Male | | Female | |
|---|---|---|---|---|---|---|
| Percentiles | ST2 (ng/mL) | 95% CI | ST2 (ng/mL) | 95% CI | ST2 (ng/mL) | 95% CI |
| 2.5 | 8.0 | 7.1 to 8.6 | 8.0 | 7.7 to 11.8 | 7.3 | 5.5 to 8.4 |
| 5 | 9.3 | 8.4 to 10.2 | 11.8 | 8.6 to 12.7 | 8.5 | 7.3 to 9.4 |
| 10 | 11.5 | 10.3 to 11.9 | 13.7 | 12.2 to 14.8 | 10.2 | 9.0 to 11.2 |
| 25 | 14.5 | 13.7 to 15.2 | 17.6 | 16.8 to 18.7 | 12.4 | 11.9 to 13.5 |
| median | 18.8 | 18.2 to 19.9 | 23.6 | 21.3 to 25.1 | 16.2 | 15.4 to 17.4 |
| 75 | 25.3 | 23.8 to 26.9 | 30.6 | 28.7 to 33.3 | 19.9 | 18.8 to 20.8 |
| 90 | 34.3 | 32.4 to 35.6 | 37.2 | 35.5 to 40.9 | 23.7 | 22.2 to 25.8 |
| 95 | 37.9 | 35.9 to 41.3 | 45.4 | 39.4 to 48.6 | 29.0 | 24.6 to 33.2 |
| 97.5 | 45.6 | 40.1 to 48.7 | 48.5 | 45.8 to 58.5 | 33.1 | 29.6 to 39.9 |

Human Soluble ST2 Concentrations in Fasting versus Non-Fasting Status: A plasma sample was drawn from twenty-five patients (19 males and 6 females) with various disease states (8 of them with type 2 diabetes mellitus) after an overnight fasting period at 7:00 a.m. The patients thereafter had a standardized breakfast (730 kcal for patients without diabetes and 522 kcal for those with diabetes). A second blood draw for human soluble ST2 determination was at 11:00 a.m. Afterwards, all patients had a standardized lunch (800 kcal for patients without diabetes, and 716 kcal for those with diabetes). The third and final blood draw was at 2:00 p.m. Mean human soluble ST2 concentrations of the 25 individuals were calculated for all three time points. Paired t-tests were used to determine whether there was a difference between the non-fasting human soluble ST2 plasma concentrations (i.e., blood withdrawal at 11:00 a.m. and 2:00 p.m.) compared with the respective fasting values (i.e., blood withdrawal at 7:00 a.m.). The relative change of human soluble ST2 concentrations in time course was compared with the RCV to estimate the effect of food on the analyte concentration.

The mean fasting human soluble ST2 concentration was 18 U/mL (median, 17 U/mL; range 9-26 U/mL) at 7:00 a.m., the mean human soluble ST2 concentration after breakfast was 19 U/mL (median, 18 U/mL; range, 11-28 U/mL; p=0.025 for comparison with fasting ST2) at 11:00 a.m., and the mean human soluble ST2 concentration after lunch was 18 U/mL (median, 18 U/mL; range, 10-28 U/mL; p=0.014 for comparison with fasting human soluble ST2) at 2:00 p.m. Mean human soluble ST2 concentrations at 11:00 a.m. and 2:00 p.m. were thus <5% higher than the mean fasting value obtained at 7:00 a.m.

Comparison of Normal Human Soluble ST2 Concentrations and Disease State Concentrations: Concentrations of human soluble ST2 were distinctly higher in patients with heart failure than in normal, healthy individuals. In the following analysis, the normal concentration as determined from the 490 healthy donors was compared to various distinct populations; 528 healthy volunteers confirmed by biomarker screening to be absent of occult cardiovascular disease (CVD) or inflammatory disease (screened by BNP, PCT, CRP, and IL-6), 709 patients diagnosed with acute heart failure, 1159 patients diagnosed with chronic, stable heart failure, 190 patients diagnosed with pulmonary arterial hypertension (PAH), 48 patients diagnosed with asthma, 223 diagnosed with asthma or COPD, 58 diagnosed with pulmonary embolism (PE), 119 diagnosed with pneumonia (PNA), 109 diagnosed with advanced respiratory disease syndrome (ARDS), 50 juveniles diagnosed with Kawasaki disease (KD), and 15 diagnosed with sepsis. Table 10 lists the median values, 95% confidence interval, and interquartile range (IQR) for human soluble ST2 concentrations in each group.

TABLE 10 sST2 Concentrations by Disease Status

| Disease State | N | Median sST2 (ng/mL) | 95% CI | IQR |
|---|---|---|---|---|
| Normal | 490 | 18.8 | 18.1-19.9 | 14.5-25.3 |
| Biomarker confirmed healthy | 528 | 11.1 | 10.4-11.7 | 7.5-16.6 |
| Chronic heart failure | 1159 | 27.4 | 26.3-29.0 | 19.3-43.0 |
| Acute heart failure | 709 | 59.8 | 55.5-63.4 | 36.1-97.2 |

TABLE 10-continued sST2 Concentrations by Disease Status

| Disease State | N | Median sST2 (ng/mL) | 95% CI | IQR |
|---|---|---|---|---|
| Pulmonary Arterial Hypertension (PAH) | 190 | 31.7 | | 22.1-51.7 |
| Kawasaki disease | 50 | 34.2 | 25.2-51.6 | 19.7-72.5 |
| ARDS | 109 | 662.0 | 481.5-1031.7 | 290.8-1846 |
| Asthma | 48 | 46.4 | 33.1-81.5 | 29.4-97.8 |
| Pulmonary embolism | 58 | 43.5 | 34.9-70.2 | 27.2-94.3 |
| COPD/Asthma | 223 | 62.8 | 55.5-73.1 | 40.2-126.2 |
| Pneumonia | 119 | 69.4 | 57.2-79.6 | 39.9-118.9 |
| Sepsis | 15 | 745 | 283-3178 | 325-2772 |

Comparison of Human Soluble ST2 Concentrations and Risk of Death at 1 Year: Concentrations of human soluble ST2 were also measured in blood samples from the PRIDE cohort (Junuzzi et al., *J. Am. Coll. Cardiol.* 50:607-613, 2007). Of the 599 subjects in the original PRIDE cohort, 586 had blood sample available for measurement of human soluble ST2 using the methods described above. The samples used were EDTA plasma aliquots frozen at −80° C. Receiver operating characteristic plots (ROC) plots with death at one year as the reference standard were analyzed and the areas under the curve (AUC) were compared according to the method by Hanley et al. (*Radiology* 148:839-843, 1983) to determining the capability of the assay for preduction of 1-year all-cause mortality in the PRIDE cohort.

In these experiments, the median concentrations for the entire cohort were 27 ng/mL (range, <2-393 ng/mL) for the assay. In this cohort, non-parametric correlation analysis revealed a correlation coefficient ($r_s$) of 0.955 (95% CI, 0.947-0.962; p<0.001) for both methods. Of the 586 patients, 92 (16%) individuals had died at one year and 494 (84%) survived. The ROC curve analyses demonstrate an AUC of 0.803 (95% CI, 0.768-0.834) by the assay for predicting death at 1 year.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody produced by the hybridoma deposited at the American Type Culture Collection (ATCC) and designated by Patent Deposit Designation PTA-10431.

2. An antigen-binding fragment of an antibody, wherein the antigen-binding fragment is a fragment of the antibody produced by the hybridoma deposited at the American Type Culture Collection (ATCC) and designated by Patent Deposit Designation PTA-10431.

3. The antibody of claim 1, wherein the antibody is labeled.

4. A hybridoma selected from the group consisting of: the hybridoma deposited at the American Type Culture Collection (ATCC) and designated by the Patent Deposit Designation PTA-10431 and the hybridoma deposited at the ATCC and designated by the Patent Deposit Designation PTA-10432.

5. A method of detecting human soluble ST2 in a sample, the method comprising:
contacting the sample with at least one antibody of claim 1; and
detecting binding of the antibody to human soluble Growth Stimulation-Expressed Gene 2 (ST2).

6. The method of claim 5, wherein the sample is from a subject who is undiagnosed or is not presenting with one or more symptoms of a disease.

7. The method of claim 5, wherein the sample is from a subject who has been diagnosed as having a disease or has been identified as being at risk of developing a disease.

8. The method of claim 7, wherein the disease is selected from the group consisting of: heart failure, coronary artery disease, cardiovascular disease, acute coronary syndrome, renal insufficiency, and stroke.

9. The method of claim 5, wherein the sample is from a subject who has one or more of: hypertriglyceridemia, hypercholesterolemia, hypertension, and a body mass index of $\geq 30$.

10. The method of claim 5, wherein the sample comprises blood, serum, or plasma.

11. A kit comprising at least one antibody of claim 1.

12. The kit of claim 11, wherein the kit is provided as an enzyme-linked immunosorbent assay.

13. The kit of claim 11, further comprising a recombinant human soluble ST2 isolated from a human cell.

14. An isolated antibody produced by the hybridoma deposited at the ATCC and designated by the Patent Deposit Designation PTA-10432.

15. The antibody of claim 14, wherein the antibody is labeled.

16. A method of detecting human soluble ST2 in a sample, the method comprising:
contacting the sample with at least one antibody of claim 14; and
detecting binding of the antibody to human soluble Growth Stimulation-Expressed Gene 2 (ST2).

17. The method of claim 16, wherein the sample is from a subject who is undiagnosed or is not presenting with one or more symptoms of a disease.

18. The method of claim 16, wherein the sample is from a subject who has been diagnosed as having a disease or has been identified as being at risk of developing a disease.

19. The method of claim 18, wherein the disease is selected from the group consisting of: heart failure, coronary artery disease, cardiovascular disease, acute coronary syndrome, renal insufficiency, and stroke.

20. The method of claim 16, wherein the sample is from a subject who has one or more of: hypertriglyceridemia, hypercholesterolemia, hypertension, and a body mass index of $\geq 30$.

21. The method of claim 16, wherein the sample comprises blood, serum, or plasma.

22. A kit comprising at least one antibody of claim 14.

23. The kit of claim 22, wherein the kit is provided as an enzyme-linked immunosorbent assay.

24. The kit of claim 22, further comprising a recombinant human soluble ST2 isolated from a human cell.

25. The antigen-binding fragment of claim 2, wherein the antigen-binding fragment has a $K_D$ for binding to human soluble Growth Stimulation-Expressed Gene 2 (ST2) equal to or less than $1.51 \times 10^{-9}$ M.

26. A chimeric or humanized antibody comprising the antigen-binding fragment of claim 2, wherein the chimeric or humanized antibody specifically binds to soluble ST2.

27. The chimeric or humanized antibody of claim 26, wherein the chimeric or humanized antibody comprises the complementary determining regions of the light and heavy chain of the antibody produced by the hybridoma deposited at the ATCC and designated by the Patent Deposit Designation PTA-10431.

28. The antigen-binding fragment of claim 2, wherein the antigen-binding fragment is selected from the group consisting of: a Fab fragment, a F(ab')$_2$ fragment, and a scFv fragment.

29. The antigen-binding fragment of claim 2, wherein the antigen-binding fragment is labeled.

30. A method of detecting human soluble ST2 in a sample, the method comprising:
contacting the sample with at least one antigen-binding fragment of claim 2; and
detecting binding of the antigen-binding fragment to human soluble Growth Stimulation-Expressed Gene 2 (ST2).

31. A kit comprising at least one antigen-binding fragment of claim 2.

32. An antigen-binding fragment of an antibody, wherein the antigen-binding fragment is a fragment of the antibody produced by the hybridoma deposited at the American Type Culture Collection (ATCC) and designated by Patent Deposit Designation PTA-10432.

33. The antigen-binding fragment of claim 32, wherein the antigen-binding fragment has a $K_D$ for binding to human soluble Growth Stimulation-Expressed Gene 2 (ST2) equal to or less than $8.59 \times 10^{-10}$ M.

34. The antigen-binding fragment of claim 32, wherein the antigen-binding fragment is selected from the group consisting of: a Fab fragment, a F(ab')$_2$ fragment, and a scFv fragment.

35. The antigen-binding fragment of claim 32, wherein the antigen-binding fragment is labeled.

36. A chimeric or humanized antibody comprising the antigen-binding fragment of claim 32, wherein the chimeric or humanized antibody specifically binds to soluble ST2.

37. The chimeric or humanized antibody of claim 36, wherein the chimeric or humanized antibody comprises the complementary determining regions of the light and heavy chain of the antibody produced by the hybridoma deposited at the ATCC and designated by the Patent Deposit Designation PTA-10432.

38. A method of detecting human soluble ST2 in a sample, the method comprising:
contacting the sample with at least one antigen-binding fragment of claim 32; and
detecting binding of the antigen-binding fragment to human soluble Growth Stimulation-Expressed Gene 2 (ST2).

39. A kit comprising at least one antigen-binding fragment of claim 32.

* * * * *

UNITED STATES PATENT AND TRADEMARK OFFICE
CERTIFICATE OF CORRECTION

PATENT NO. : 8,420,785 B2  
APPLICATION NO. : 13/083333  
DATED : April 16, 2013  
INVENTOR(S) : Snider Page 1 of 1

It is certified that error appears in the above-identified patent and that said Letters Patent is hereby corrected as shown below:

In the Claims

Column 49, Line 31, Claim 13, delete "ST2isolated" and insert -- ST2 isolated --;

Column 49, Line 63, Claim 24, delete "ST2isolated" and insert -- ST2 isolated --.

Signed and Sealed this
Seventh Day of January, 2014

Margaret A. Focarino
*Commissioner for Patents of the United States Patent and Trademark Office*